US009763703B2

(12) United States Patent
Black et al.

(10) Patent No.: US 9,763,703 B2
(45) Date of Patent: Sep. 19, 2017

(54) CROSS CONNECTORS, KITS, AND METHODS

(71) Applicant: DeGen Medical, Inc., Florence, SC (US)

(72) Inventors: Craig Black, Florence, SC (US); Kidong Yu, Florence, SC (US)

(73) Assignee: DeGen Medical, Inc., Florence, SC (US)

( * ) Notice: Subject to any disclaimer, the term of this patent is extended or adjusted under 35 U.S.C. 154(b) by 122 days.

(21) Appl. No.: 14/704,655

(22) Filed: May 5, 2015

(65) Prior Publication Data

US 2016/0324545 A1 Nov. 10, 2016

(51) Int. Cl.
*A61B 17/70* (2006.01)

(52) U.S. Cl.
CPC .................. *A61B 17/7052* (2013.01)

(58) Field of Classification Search
CPC .................................. A61B 17/7042
USPC ........................................ 606/252
See application file for complete search history.

(56) References Cited

U.S. PATENT DOCUMENTS

| | | |
|---|---|---|
| 5,584,831 A | 12/1996 | McKay |
| 5,980,523 A | 11/1999 | Jackson |
| 6,050,997 A | 4/2000 | Mullanem |
| 6,083,226 A | 7/2000 | Fiz |
| 6,136,000 A | 10/2000 | Louis et al. |
| 6,139,548 A | 10/2000 | Errico |
| 6,217,578 B1 | 4/2001 | Crozet et al. |
| 6,283,967 B1 | 9/2001 | Troxell et al. |
| 6,287,311 B1 | 9/2001 | Sherman et al. |
| 6,402,751 B1 | 6/2002 | Hoeck et al. |
| 6,413,257 B1 | 7/2002 | Lin et al. |
| 6,413,258 B1 | 7/2002 | Bernhardt, Jr. |
| 6,416,515 B1 | 7/2002 | Wagner |
| 6,471,703 B1 | 10/2002 | Ashman |
| 6,524,310 B1 | 2/2003 | Lombardo et al. |
| 6,562,040 B1 | 5/2003 | Wagner |
| 6,602,253 B2 | 8/2003 | Richelsoph et al. |
| 6,736,817 B2 | 5/2004 | Troxell et al. |
| 6,749,612 B1 | 6/2004 | Conchy et al. |
| 6,749,614 B2 | 6/2004 | Teitelbaum et al. |
| 6,783,526 B1 | 8/2004 | Lin et al. |
| 6,793,657 B2 | 9/2004 | Lee et al. |
| 6,866,664 B2 | 3/2005 | Schar et al. |
| 6,872,208 B1 | 3/2005 | McBride et al. |
| 6,881,215 B2 | 4/2005 | Assaker et al. |
| 7,029,474 B2 | 4/2006 | Richelsoph et al. |
| 7,104,993 B2 | 9/2006 | Baynham et al. |
| 7,122,036 B2 | 10/2006 | Vanacker |
| 7,329,258 B2 | 2/2008 | Studer |
| 7,559,942 B2 | 7/2009 | Paul et al. |
| 7,585,299 B2 | 9/2009 | Rezach |
| 7,628,799 B2 | 12/2009 | Richelsoph et al. |

(Continued)

*Primary Examiner* — Pedro Philogene
*Assistant Examiner* — David C Comstock
(74) *Attorney, Agent, or Firm* — Buchanan Van Tuinen LLC

(57) ABSTRACT

Cross connectors, kits, and methods useful in the treatment of bones, such as vertebrae, are described herein. An example cross connector is comprised of a first member, a second member, a saddle, a locking member, and a stop member. The first member is pivotally, rotatably, and slidably moveable within a passageway defined by the second member.

20 Claims, 12 Drawing Sheets

(56) References Cited

U.S. PATENT DOCUMENTS

| | | |
|---|---|---|
| 7,699,874 B2 | 4/2010 | Young |
| 7,717,939 B2 | 5/2010 | Ludwig et al. |
| 7,717,940 B2 | 5/2010 | Woods et al. |
| 7,736,370 B2 | 6/2010 | Sweeney |
| 7,744,633 B2 | 6/2010 | Berrevoets et al. |
| 7,771,474 B2 | 8/2010 | Cordaro |
| 7,803,174 B2 | 9/2010 | Denis et al. |
| 7,806,912 B2 | 10/2010 | Lawton et al. |
| 7,833,248 B2 | 11/2010 | Markworth et al. |
| 7,837,714 B2 | 11/2010 | Drewry et al. |
| 7,867,255 B2 | 1/2011 | Miller et al. |
| 7,901,433 B2 | 3/2011 | Forton et al. |
| 7,909,854 B2 | 3/2011 | Schwab |
| 7,927,355 B2 | 4/2011 | Berrevoets et al. |
| 7,959,653 B2 | 6/2011 | Thramann et al. |
| 7,967,845 B2 | 6/2011 | Lauryssen et al. |
| 8,021,400 B2 | 9/2011 | Marino et al. |
| 8,029,543 B2 | 10/2011 | Young et al. |
| 8,043,338 B2 | 10/2011 | Dant |
| 8,052,726 B2 | 11/2011 | Nayet et al. |
| 8,080,037 B2 | 12/2011 | Butler et al. |
| 8,109,976 B2 | 2/2012 | Lim et al. |
| 8,118,837 B2 | 2/2012 | Lemoine |
| 8,137,388 B2 | 3/2012 | Sasing et al. |
| 8,182,516 B2 | 5/2012 | Winslow et al. |
| 8,197,515 B2 | 6/2012 | Levy et al. |
| 8,221,466 B2 | 7/2012 | Asaad et al. |
| 8,241,334 B2 | 8/2012 | Butler et al. |
| 8,246,657 B1 | 8/2012 | Samuel |
| 8,277,489 B2 | 10/2012 | Saidha et al. |
| 8,313,514 B2 | 11/2012 | Puno |
| 8,337,532 B1 | 12/2012 | McLean et al. |
| 8,353,934 B2 | 1/2013 | Drewry et al. |
| 8,361,117 B2 | 1/2013 | Michielli et al. |
| 8,366,749 B2 | 2/2013 | Sweeney |
| 8,372,119 B2 | 2/2013 | Kim et al. |
| 8,398,681 B2 | 3/2013 | Augostino et al. |
| 8,460,342 B2 | 6/2013 | Courtney et al. |
| RE44,392 E | 7/2013 | Hynes |
| 8,475,499 B2 | 7/2013 | Cournoyer et al. |
| 8,480,713 B2 | 7/2013 | Rezach |
| 8,491,642 B2 | 7/2013 | Marino et al. |
| 8,591,550 B2 | 11/2013 | Ludwig et al. |
| 8,608,781 B2 | 12/2013 | Asaad et al. |
| 8,617,213 B2 | 12/2013 | Moore et al. |
| 8,657,855 B2 | 2/2014 | Zhang |
| 8,672,978 B2 | 3/2014 | Dant et al. |
| 8,728,124 B2 | 5/2014 | Miller |
| 8,771,319 B2 | 7/2014 | Prajapati |
| 8,784,452 B2 | 7/2014 | Saidha et al. |
| 8,808,328 B2 | 8/2014 | Hwang |
| 8,814,909 B2 | 8/2014 | Fanger et al. |
| 8,828,055 B2 | 9/2014 | Blain et al. |
| 8,828,056 B2 | 9/2014 | Buss et al. |
| 8,828,061 B2 | 9/2014 | Scrantz et al. |
| 8,864,798 B2 | 10/2014 | Weiman et al. |
| 8,864,799 B2 | 10/2014 | Kraus |
| 8,870,921 B2 | 10/2014 | Michielli et al. |
| 8,870,922 B2 | 10/2014 | Hammer |
| 8,870,923 B2 | 10/2014 | Richelsoph |
| 8,876,871 B2 | 11/2014 | Black |
| 8,920,471 B2 | 12/2014 | Barrus et al. |
| 8,940,021 B2 | 1/2015 | James |
| 8,945,186 B2 | 2/2015 | Walker et al. |
| 2005/0228377 A1* | 10/2005 | Chao .................. A61B 17/7052 606/252 |
| 2008/0172093 A1 | 7/2008 | Nilsson |
| 2008/0234736 A1 | 9/2008 | Trieu et al. |
| 2008/0306516 A1 | 12/2008 | Winslow et al. |
| 2008/0306549 A1 | 12/2008 | Winslow et al. |
| 2009/0326588 A1 | 12/2009 | Felix et al. |
| 2010/0241168 A1 | 9/2010 | Franck et al. |
| 2010/0305612 A1 | 12/2010 | Nilsson |
| 2011/0071569 A1 | 3/2011 | Black |
| 2012/0226316 A1 | 9/2012 | Dant et al. |
| 2012/0253397 A1 | 10/2012 | Kraus |
| 2013/0116731 A1 | 5/2013 | Michielli et al. |
| 2013/0131727 A1 | 5/2013 | Kim et al. |
| 2013/0268003 A1 | 10/2013 | Hwang |
| 2013/0268004 A1 | 10/2013 | Rathbun |
| 2013/0274801 A1 | 10/2013 | Buss et al. |
| 2014/0148858 A1 | 5/2014 | Dant et al. |
| 2014/0200615 A1 | 7/2014 | Yeh |
| 2014/0277145 A1 | 9/2014 | Reitblat et al. |
| 2014/0277146 A1 | 9/2014 | Li et al. |
| 2014/0288603 A1 | 9/2014 | Black |
| 2014/0316468 A1 | 10/2014 | Keiser et al. |
| 2014/0336706 A1 | 11/2014 | Garamszegi |
| 2015/0005822 A1 | 1/2015 | Weiman et al. |
| 2015/0025576 A1 | 1/2015 | Taylor |

* cited by examiner

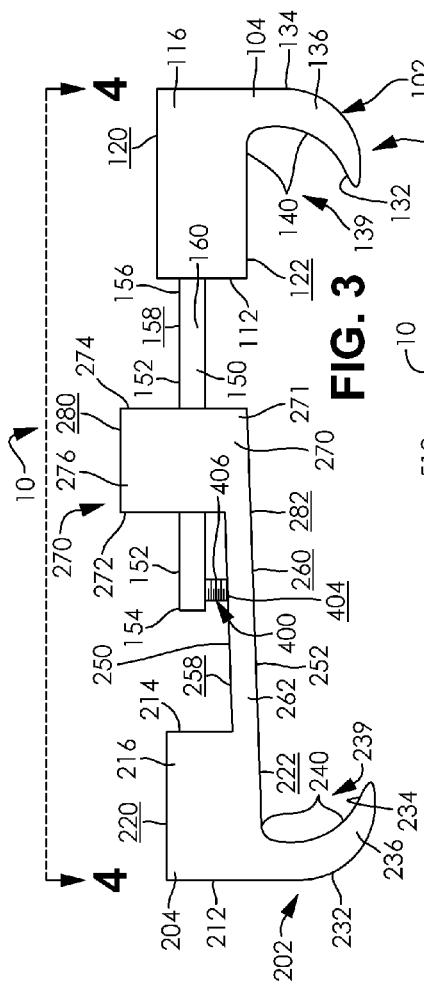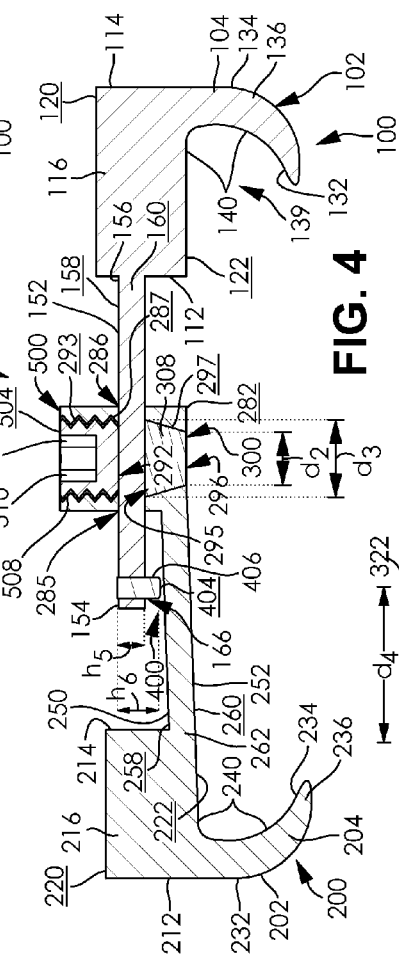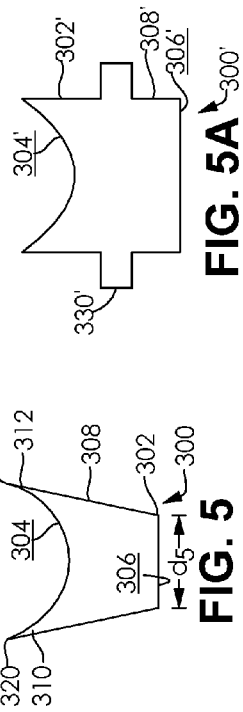

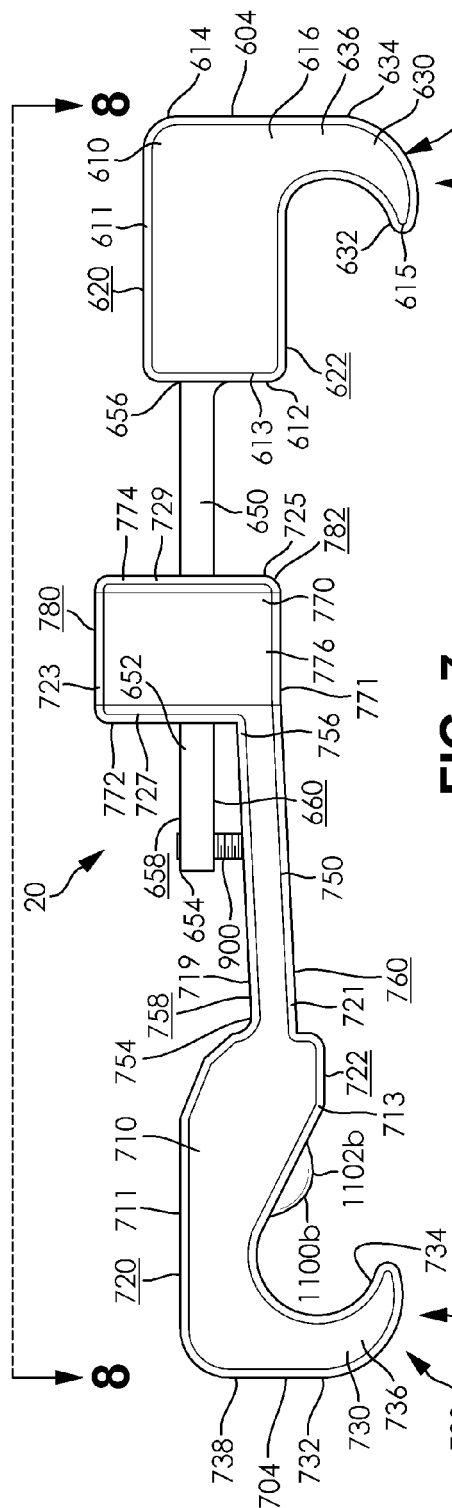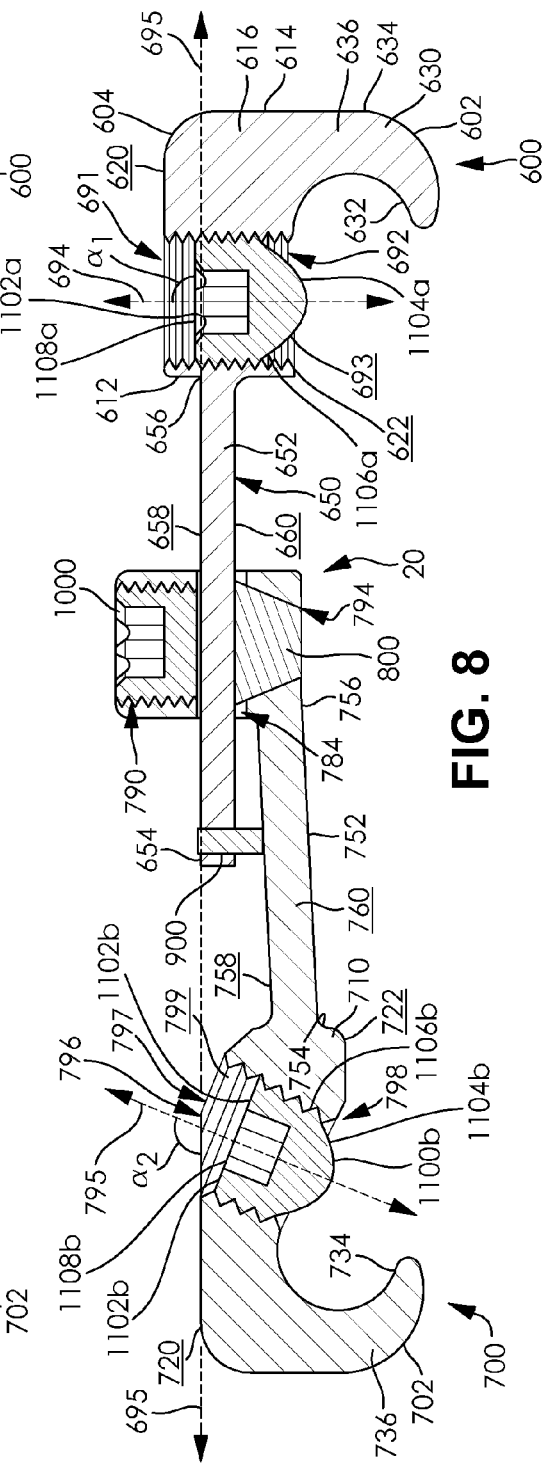
FIG. 7
FIG. 8

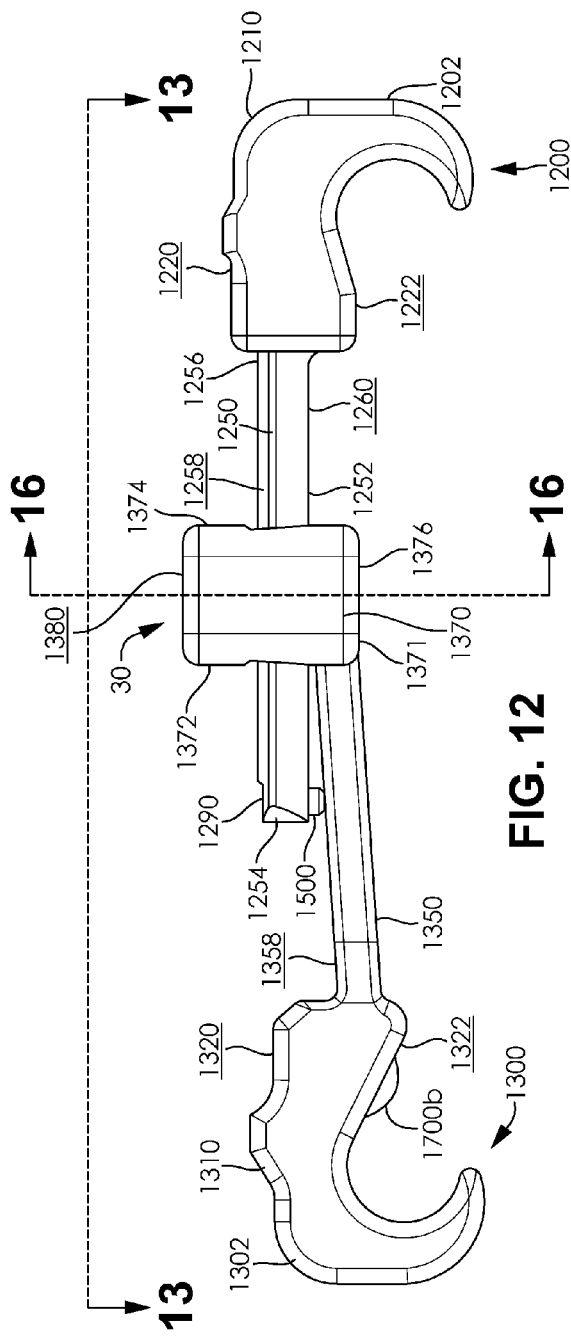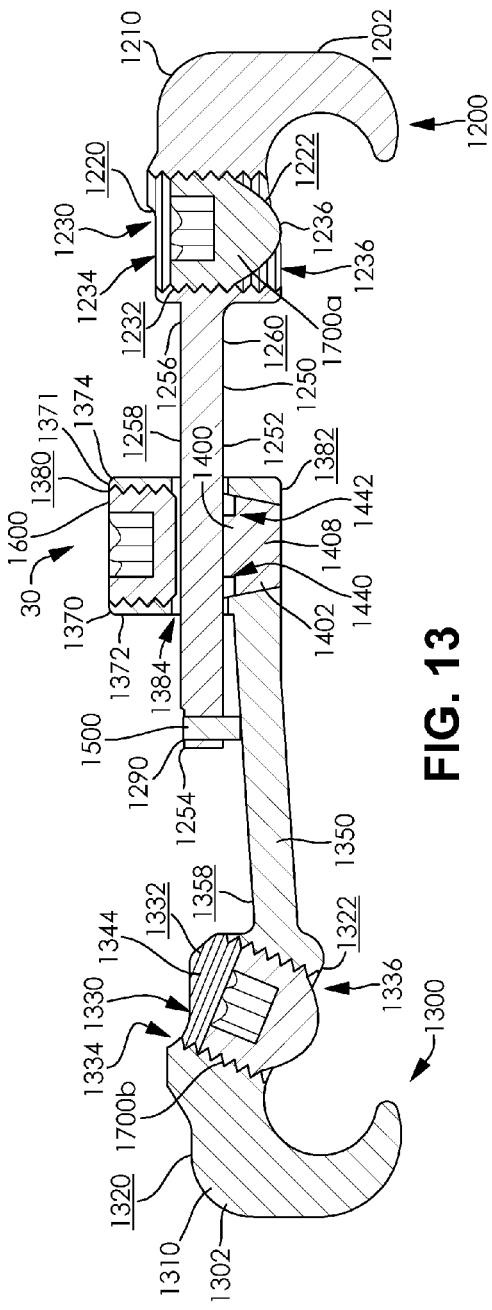

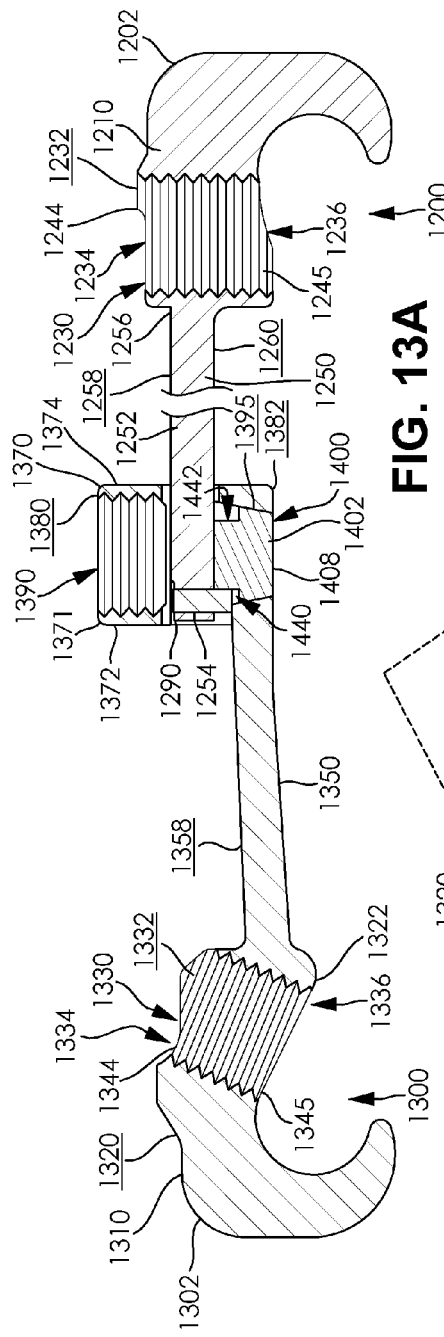
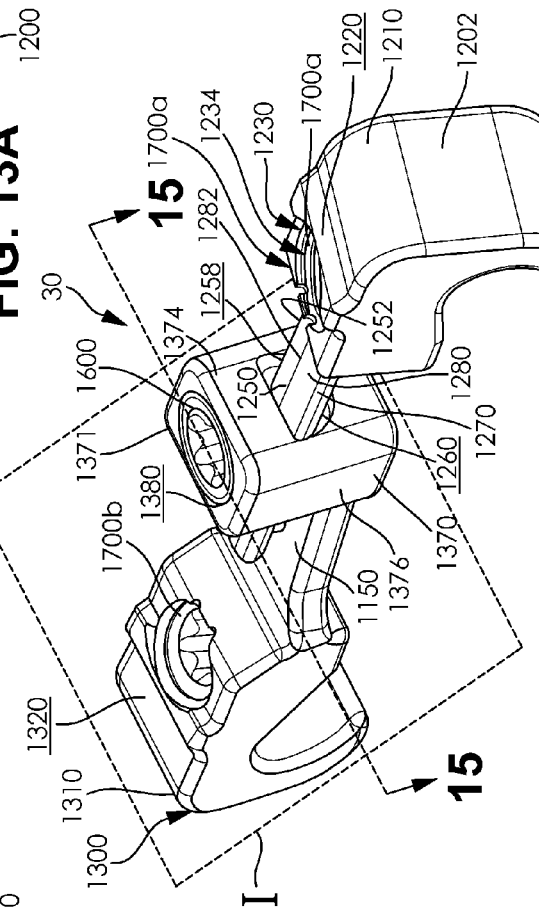
FIG. 13A
FIG. 14

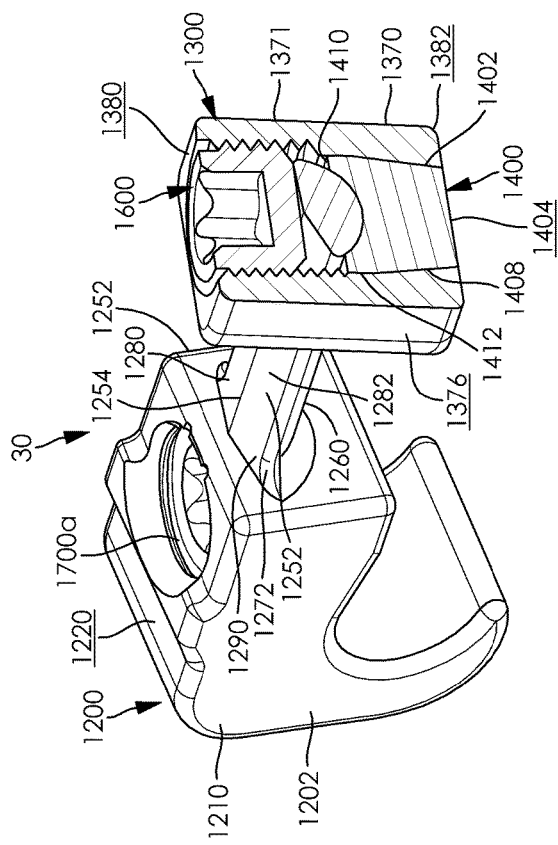
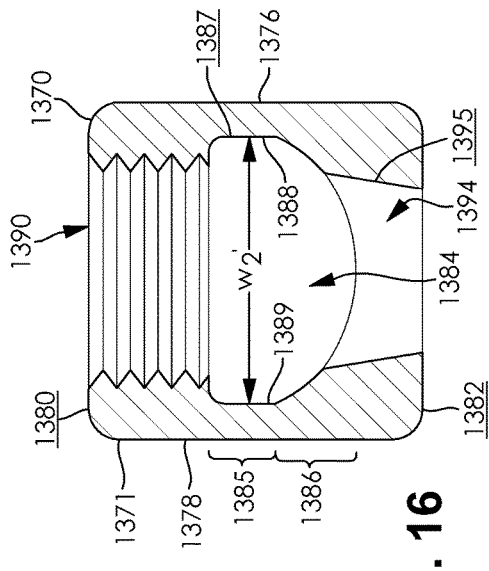
FIG. 15
FIG. 16

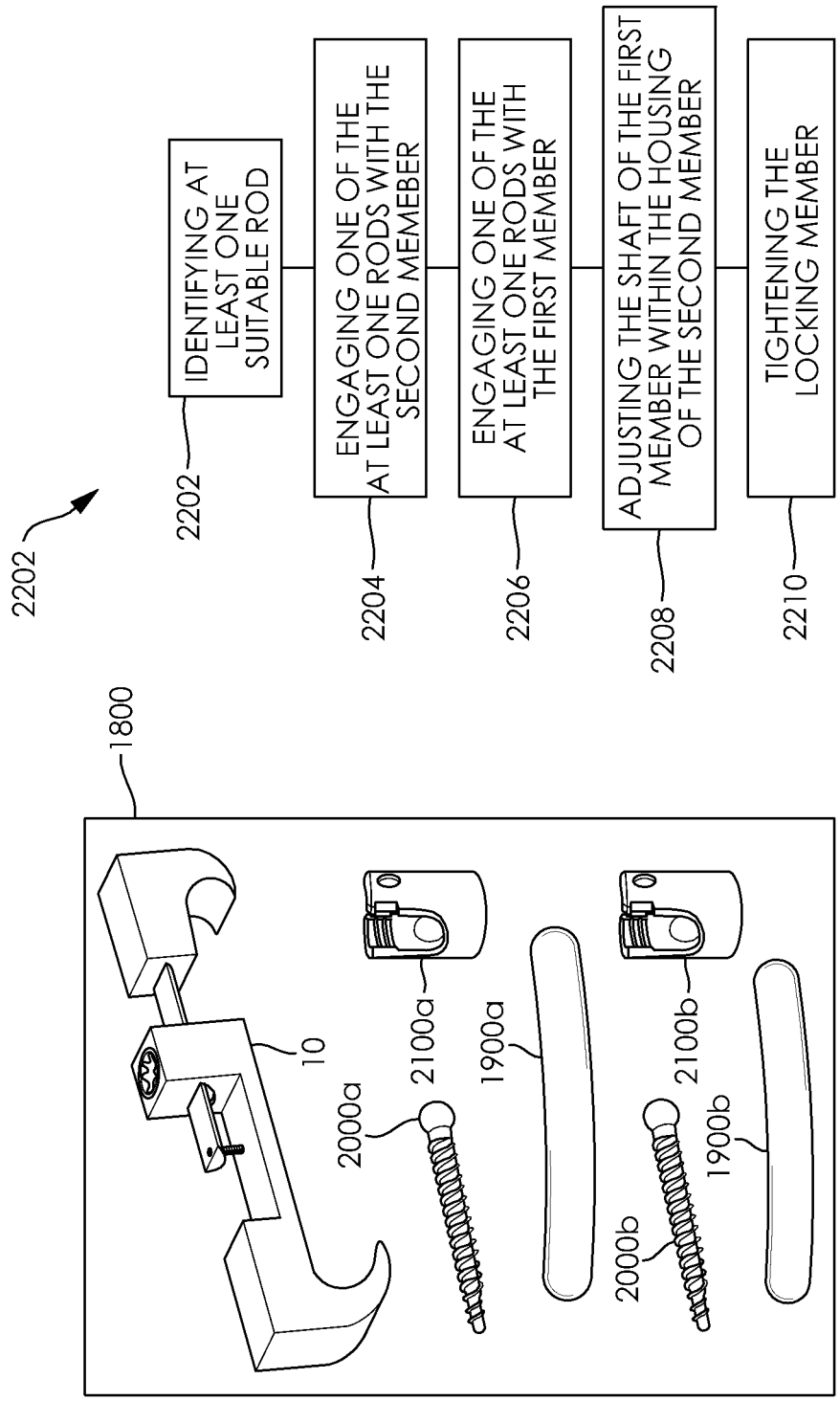

CROSS CONNECTORS, KITS, AND METHODS

FIELD

The disclosure relates to the technical field of apparatuses, kits, and methods useful in the treatment of bones, such as vertebrae. More specifically, cross connectors, kits, and methods useful for connecting medical devices that are directly or indirectly attached to bones in an animal, such as a human, are described herein.

BACKGROUND

The art includes several examples of cross connectors, kits, and methods useful for connecting medical devices directly or indirectly attached to bones to each other through the use of a cross connector.

Several designs, for example, include cross connectors that connect multiple rods engaged with anchors implanted within bones or portions of bones. In one example, described in U.S. Pat. No. 7,717,940, a cross connector connects two rods and provides multiple adjustment options.

Despite this and other examples, a need exists for improved cross connectors, kits, and methods.

BRIEF SUMMARY OF EXAMPLES

Various example cross connectors are described and illustrated herein.

An example cross connector configured to engage at least one medical device comprises a first member having an arm and a shaft, the arm being configured to engage one of said at least one medical device, the shaft having an upper surface and a lower surface, the shaft defining a channel extending from the upper surface to the lower surface, the upper surface of the shaft having a first width; a second member having an arm, a housing, and a shaft, the shaft extending from the arm to the housing, the shaft having an upper surface, the arm being configured to engage one of said at least one medical device, the housing having a proximal side, a distal side, an upper surface, a passageway, a channel, and a void, the passageway extending from the proximal side to the distal side and defining a first opening and a second opening, the first opening having a second width, the channel at least partially defined by the upper surface and in communication with the passageway, the void in communication with the passageway, the shaft of the first member disposed within the passageway such that the first member is rotatably, pivotally, and slidably moveable within the passageway; a saddle, the saddle housed within the void of the housing of the second member and configured to engage the shaft of the first member, the saddle being rotatable; a stop member, the stop member disposed within the channel of the shaft of the first member; and a locking member, the locking member disposed within the channel of the housing of the second member such that the locking member is in contact with the upper surface of the shaft of the first member; the first width is less than the second width.

Another example cross connector configured to engage at least one medical device comprises a first member having an arm and a shaft, the arm being configured to engage one of said at least one medical device, the arm having an upper arm surface and a lower arm surface, the arm defining a first arm channel extending from the upper arm surface to the lower arm surface, the shaft having an upper surface and a lower surface, the shaft defining a channel extending from the upper surface to the lower surface, the upper surface of the shaft having a first width; a second member having an arm, a housing, and a shaft, the shaft extending from the arm to the housing, the shaft having an upper surface, the arm being configured to engage one of said at least one medical device, the arm having an upper arm surface and a lower arm surface, the arm defining a second arm channel extending from the upper arm surface to the lower arm surface, the housing having a proximal side, a distal side, an upper surface, a passageway, a channel, and a void, the passageway extending from the proximal side to the distal side and defining a first opening and a second opening, the first opening having a second width, the channel at least partially defined by the upper surface and in communication with the passageway, the void in communication with the passageway, the shaft of the first member disposed within the passageway such that the first member is rotatably, pivotally, and slidably moveable within the passageway; a saddle, the saddle housed within the void of the housing of the second member and configured to engage the shaft of the first member, the saddle being rotatable and having an upper surface, a lower surface, and a side that tapers from the upper surface to the lower surface, the side and the upper surface cooperatively defining first and second cavities; a stop member, the stop member disposed within the channel of the shaft of the first member; and a locking member, the locking member disposed within the channel of the housing of the second member such that the locking member is in contact with the upper surface of the shaft of the first member; the first width is less than the second width.

Another example cross connector configured to engage at least one medical device comprises a first member having an arm and a shaft, the arm being configured to engage one of said at least one medical device, the arm having an upper arm surface and a lower arm surface, the arm defining a first arm channel extending from the upper arm surface to the lower arm surface, the shaft having an upper surface and a lower surface, the shaft defining a channel extending from the upper surface to the lower surface, the upper surface of the shaft having a first width; a second member having an arm, a housing, and a shaft, the shaft extending from the arm to the housing, the shaft having an upper surface, the arm being configured to engage one of said at least one medical device, the arm having an upper arm surface and a lower arm surface, the arm defining a second arm channel extending from the upper arm surface to the lower arm surface, the housing having a proximal side, a distal side, an upper surface, a passageway, a channel, and a void, the passageway extending from the proximal side to the distal side and defining a first opening and a second opening, the first opening having a second width, the channel at least partially defined by the upper surface and in communication with the passageway, the void in communication with the passageway, the shaft of the first member disposed within the passageway such that the first member is rotatably, pivotally, and slidably moveable within the passageway; a saddle, the saddle housed within the void of the housing of the second member and configured to engage the shaft of the first member, the saddle being rotatable and having an upper surface, a lower surface, and a side that tapers from the upper surface to the lower surface, the side and the upper surface cooperatively defining first and second cavities; a stop member, the stop member disposed within the channel of the shaft of the first member; a locking member, the locking member disposed within the channel of the housing of the second member such that the locking member is in contact with the upper surface of the shaft of the first member; a first set screw disposed within the first arm channel; and a second set screw disposed within the second arm channel; the first width is less than the second width.

Additional understanding of the cross connectors, kits, and methods can be obtained with review of the detailed description, below, and the appended drawings.

DESCRIPTION OF FIGURES

FIG. 3 is a side view of the cross connector illustrated in FIG. 1.

FIG. 4 is a sectional view of the cross connector illustrated in FIG. 1, taken along line 4-4 in FIG. 3.

FIG. 5 is a magnified side view of the saddle illustrated in FIG. 2.

FIG. 5A is a magnified side view of an alternative saddle.

FIG. 7 is a side view of the cross connector illustrated in FIG. 6.

FIG. 8 is a sectional view of the cross connector illustrated in FIG. 6, taken along line 8-8 in FIG. 7.

FIG. 12 is a side view of the cross connector illustrated in FIG. 10.

FIG. 13 is a sectional view of the cross connector illustrated in FIG. 10, taken along line 13-13 in FIG. 12. The cross connector is illustrated in a first configuration.

FIG. 13A is a side view of the cross connector illustrated in FIG. 13. The cross connector is illustrated in a second configuration and without the set screws and the locking member illustrated in FIG. 13.

FIG. 14 is another perspective view of the cross connector illustrated in FIG. 10.

FIG. 15 is a magnified sectional view of Area I of the cross connector illustrated in FIG. 14, taken along line 15-15.

FIG. 16 is a magnified sectional view of the cross connector illustrated in FIG. 10, taken along line 16-16 in FIG. 12. The cross connector is illustrated without the first member and the locking member illustrated in FIG. 10 and without a saddle.

FIG. 20 is a schematic illustration of an example kit.

FIG. 21 is a flowchart representation of an example method of engaging a cross connector with at least one rod.

DESCRIPTION OF EMBODIMENTS

Figure 1:
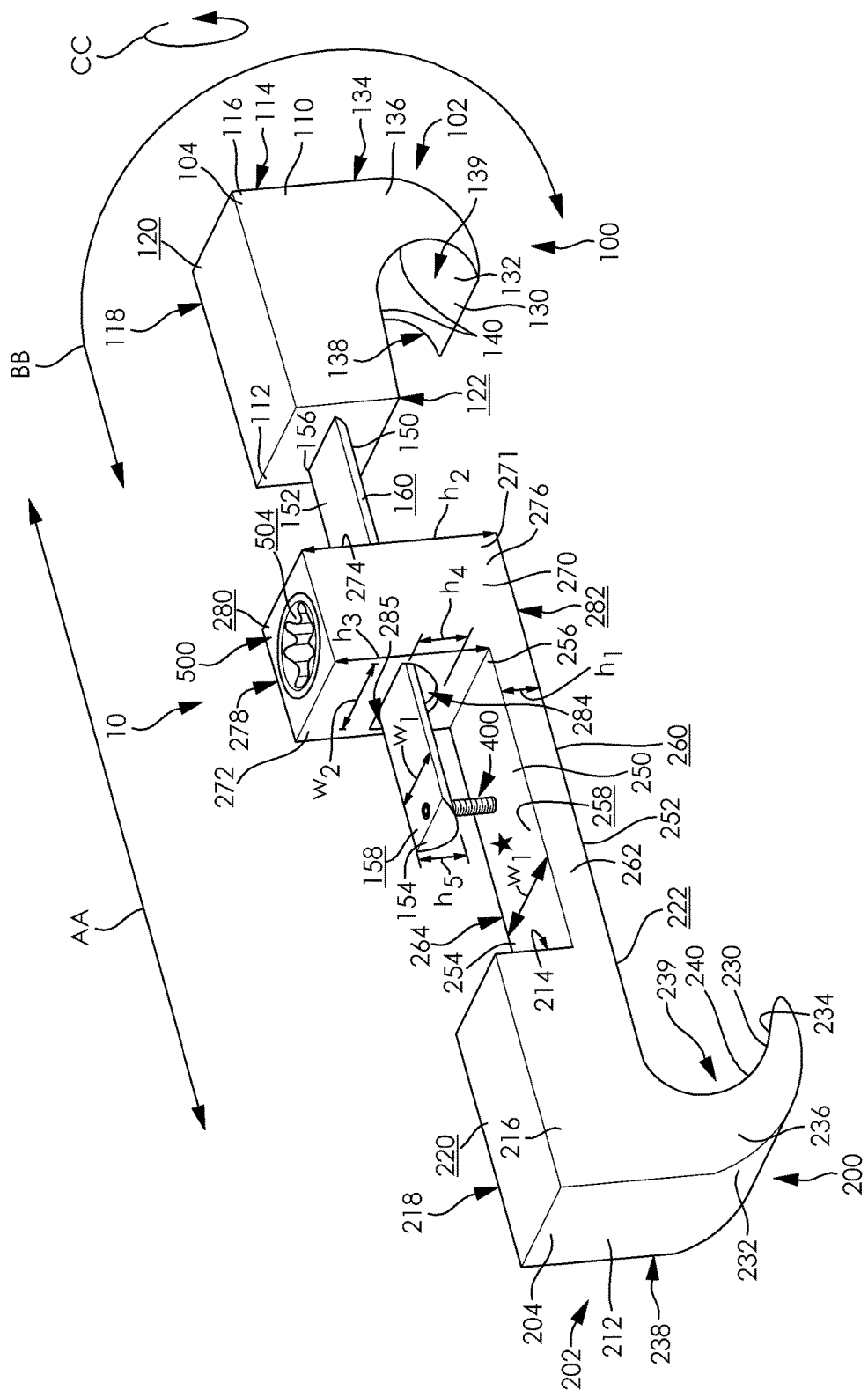
FIG. 1 is a perspective view of an example cross connector.

The following detailed description and the appended drawings describe and illustrate various example embodiments. The description and illustration of these examples are provided to enable one skilled in the art to make and use cross connectors, kits, and methods. They are not intended to limit the scope of the claims in any manner.

In the drawings and the description, a reference number followed by a lower case letter, e.g., 1100a, refers to a specific structure that is a member of a group of related structures that are denoted by the same reference number but with a different letter, e.g., 1100b. For example, in FIG. 8, the set screws are indicated by reference numbers 1100a and 1100b.

Each of FIGS. 1, 2, 3, 4, and 5 illustrates a first example cross connector 10 or component thereof. FIG. 5A illustrates an alternative saddle 300'. The cross connector 10 includes a first member 100, a second member 200, a saddle 300, a stop member 400, and a locking member 500.

The first member 100 comprises an arm 102 and a shaft 150.

The arm 102 is comprised of a main body 104 having a base 110 and a grip 130. The base 110 includes a proximal side 112, a distal side 114 opposite the proximal side 112, a first lateral side 116, a second lateral side 118 opposite the first lateral side 116, an upper surface 120, and a lower surface 122. The grip 130 comprises a proximal side 132, a distal side 134 opposite the proximal side 132, a first lateral side 136, and a second lateral side 138 disposed opposite the first lateral side 136.

The base 110 of the main body 104 is substantially box-shaped. As such, the proximal side 112 and distal side 114 are each substantially square in shape and are equal in size to one another. Each of the first lateral side 116 and second lateral side 118 are substantially rectangular in shape and are equal in size to one another. Additionally, the upper surface 120 is substantially rectangular in shape and is adjacent each of the proximal, distal, first lateral, and second lateral sides 112, 114, 116, 118. A skilled artisan will be able to determine suitable shapes and sizes for each of the proximal, distal, first lateral, and second lateral sides and the upper surface according to a particular example based on various considerations, including the device to which the cross connector will be attached and the location in the body at which the cross connector will be implanted. In an alternative embodiment, any of the proximal, distal, first lateral, and second lateral sides may have any shape, including square, rectangular, elliptical, triangular, and circular. Any of the proximal, distal, first lateral, or second lateral sides may have the same shape or a different shape than any other side, as well. In a different embodiment, the upper surface may have any shape, including square, rectangular, elliptical, triangular, and circular. In addition, the upper surface may have the same shape and size or a different shape and size as any of the proximal, distal, first lateral, or second lateral sides.

The distal side 134, the first lateral side 136, and the second lateral side 136 of the grip 130 are disposed, respectively, adjacent the distal side 114, the first lateral side 116, and the second lateral side 118. The distal side 134 is curved from where it is adjacent the distal side 114 of the base 110 to where it is adjacent the proximal side 132 of the grip 130. Each of the first lateral side 136 and the second lateral side 138 is adjacent the proximal side 132, the distal side 134, and one of the first lateral side 116 or the second lateral side 118, respectively. Each of the first lateral side 136, the second lateral side 138, and the proximal side 132 is substantially c-shaped and is disposed such that the void 139 cooperatively defined by the first and second lateral sides 136, 138 and the proximal side 132 of the grip 130 is disposed adjacent the lower surface 122 of the base 110. The lower surface 122 of the base 110 and the proximal side 132 of the grip 130 cooperatively define a gripping portion 140, which is configured to engage a medical device, such as a rod (not illustrated in the Figures), that has been implanted within a body. In the illustrated embodiment, the grip 130 is integrally formed with the base 110 to form the arm 102. A skilled artisan will be able to determine suitable shapes and sizes for each of the proximal, distal, first lateral, and second lateral sides of the grip and for the gripping portion according to a particular example based on various considerations, including the device to which the cross connector will be attached and the location in the body at which the cross connector will be implanted. In an alternative embodiment, the first and second lateral sides and the proximal side of the arm may form a portion having any shape, including circular, elliptical, and u-shaped, or form a platform that can engage a medical device, such as a rod. In a different embodiment, the first lateral side, the second lateral side, the proximal side, and the distal side of the arm may cooperatively define a c-shaped grip that is a mirror image of the c-shaped grip illustrated in the Figures. Though the first lateral portion 136 and the second lateral portion 138 have substantially the same size and shape in the illustrated embodiment, in another embodiment the first lateral portion may be larger than or smaller than the second lateral portion and may be shaped differently than the second lateral portion. Additionally, in alternative embodiments, the base and the grip may be attached to one another via an adhesive or a mechanical attachment, for example, rather than integrally formed. In other embodiments, the arm may define a channel configured to house a set screw or other locking member, which may contact the medical device that is to be engaged with the arm and assist the arm in holding the medical device in place.

The shaft 150 of the first member 100 comprises a main body 152 extending from a proximal end 154 to a distal end 156. The main body 152 has an upper surface 158 and a lower surface 160 and defines a channel 162 extending from the upper surface 158 to the lower surface 160.

In the illustrated embodiment, the shaft 150 is elongate and substantially semicircular in shape. The upper surface 158 lies on a plane that is parallel to the plane (neither plane is illustrated in the Figures) on which the upper surface 120 of the base 110 is disposed. The lower surface 160 is substantially c-shaped. Additionally, the upper surface 158 of the shaft 150 defines a first width $w_1$ that is constant from the proximal end 154 to the distal end 156; the shaft also defines a fifth height $h_5$ that is constant from the proximal end 154 to the distal end 156. A skilled artisan will be able to determine a suitable shape for the shaft and a suitable first width and fifth height according to a particular example based on various considerations, including the device to which the cross connector will be attached and the location in the body at which the cross connector will be implanted. In another embodiment, the shaft may have any shape, including that of a rod, cone, and box. In other embodiments, the shaft may taper from the proximal end to the distal end, or may taper from the distal end to the proximal end. In different embodiments, the fifth height may be greater than, equal to, about equal to, or less than the first width of the upper surface. Either of the first width or the fifth height may increase or decrease from the proximal end to the distal end.

The distal end 156 of the shaft 150 is disposed adjacent and in contact with the proximal end 112 of the base 110 of the arm 102. The upper surface 158 is disposed on a plane that is substantially perpendicular to the plane (not illustrated in the Figures) on which the proximal end 112 is disposed. Additionally, the shaft 150 is integrally formed with the arm 102 and extends away from the distal end 114 of the base 110. A skilled artisan will be able to determine how to suitably dispose the shaft with regard to the arm according to a particular example based on various considerations, including the device to which the cross connector will be attached and the location in the body at which the cross connector will be implanted. In an alternative embodiment, shaft may be disposed on a plane that is disposed at an angle to the plane on which the proximal end of the base is disposed. In a different embodiment, the shaft may not be integrally formed with the arm, and instead may be attached to the arm via an adhesive or a mechanical attachment. In other embodiments, the shaft may be attached to another portion of the arm, including one of the first or second lateral sides of the base.

The channel 162 of the shaft 150 is disposed adjacent the proximal end 154 and includes an upper opening 164 defined by the upper surface 158 and a lower opening 166 defined by the lower surface 160. In the illustrated embodiment, each of the upper opening 164 and the lower opening 166 is substantially circular in shape and has substantially the same diameter (not illustrated in the Figures). Each of the upper opening 164 and the lower opening 166 are disposed about the central axis (not illustrated in the Figures) of the channel 162. Furthermore, the inner surface 168 of the channel 162 is threaded. A skilled artisan will be able to determine how to suitably size and shape the channel and its upper and lower openings according to a particular example based on various considerations, including the shape and size of the second member and the location in the body at which the cross connector will be implanted. In alternative embodiments, each of the upper and lower openings may have any shape, including triangular, elliptical, square, and rectangular. Additionally, the upper opening may have a different shape than the lower opening and may also have a larger or smaller diameter than the lower opening. The channel may also be disposed on a plane that is parallel or angled relative to the longitudinal axis of the shaft. In other embodiments, the inner surface of the channel may not be threaded.

The second member 200 comprises an arm 202, a shaft 250, and a housing 270.

The arm 202 is comprised of a main body 204 having a base 210 and a grip 230. The base 210 includes a proximal side 212, a distal side 214 opposite the proximal side 212, a first lateral side 216, a second lateral side 218 opposite the first lateral side 216, an upper surface 220, and a lower surface 222. The grip 230 comprises a proximal side 232, a distal side 234 opposite the proximal side 232, a first lateral side 236, and a second lateral side 238 disposed opposite the first lateral side 236.

The base 210 of the main body 204 is substantially box-shaped. As such, the proximal side 212 and distal side 214 are substantially square in shape and are equal in size to one another. The first lateral side 216 and the second lateral side 218 are substantially rectangular in shape and are equal in size to one another. Additionally, the upper surface 220 is substantially rectangular in shape and is adjacent each of the proximal, distal, first lateral, and second lateral sides 212, 214, 216, 218. A skilled artisan will be able to determine suitable shapes and sizes for the proximal, distal, first lateral, and second lateral sides and the upper surface according to a particular example based on various considerations, including the device the cross connector will engage and the location in the body at which the cross connector will be implanted. In an alternative embodiment, any of the proximal, distal, first lateral, and second lateral sides may have any shape, including square, rectangular, elliptical, triangular, and circular. Any of the proximal, distal, first lateral, or second lateral sides may have the same shape as or a different shape than any other side in various embodiments, as well. In a different embodiment, the upper surface may have any shape, including square, rectangular, elliptical, triangular, and circular. The upper surface, additionally, may have the same shape and size or a different shape and size as any of the proximal, distal, first lateral, or second lateral sides.

The proximal side 232, the first lateral side 236, and the second lateral side 236 of the grip 230 are disposed, respectively, adjacent the proximal side 212, the first lateral side 216, and the second lateral side 218 of the base 210. The proximal side 232 is curved from where it is adjacent the proximal side 212 of the base 210 to where it is adjacent the distal side 234 of the grip 230. Each of the first lateral side 236 and the second lateral side 238 is adjacent the proximal side 232, the distal side 234, and one of the first lateral side 216 or the second lateral side 218 of the base 210, respectively. Each of the first lateral side 236, the second lateral side 238, and the distal side 234 is substantially c-shaped and is disposed such that the void 239 cooperatively defined by the first and second lateral sides 236, 238 and the distal side 234 of the grip 230 is disposed adjacent the lower surface 222 of the base 210. The lower surface 222 of the base 210 and the distal side 234 of the grip 230 cooperatively define a gripping portion 240, which is configured to engage a medical device, such as a rod (not illustrated in the Figures), that has been implanted within a body. In the illustrated embodiment, the grip 230 is integrally formed with the base 210 to form the arm 202. A skilled artisan will be able to determine suitable shapes and sizes for each of the proximal, distal, first lateral, and second lateral sides of the grip and the gripping portion according to a particular example based on various considerations, including the device the cross connector will engage and the location in the body at which the cross connector will be implanted. In an alternative embodiment, the first and second lateral sides and the distal side of the arm may define a portion having any shape, including circular, elliptical, and u-shaped, or form a platform that can engage a medical device, such as a rod. In a different embodiment, the first lateral side, second lateral side, proximal side, and distal side of the arm may cooperatively define a c-shaped grip that is a mirror image of the c-shaped grip illustrated in the Figures. Though the first lateral portion 236 and the second lateral portion 238 have substantially the same size and shape in the illustrated embodiment, in another embodiment the first lateral portion may be larger than or smaller than the second lateral portion and may be shaped differently than the second lateral portion. Additionally, in alternative embodiments, the base and the grip may be attached to one another via an adhesive or a mechanical attachment, for example, rather than integrally formed. In other embodiments, the arm may define a channel configured to house a set screw or other locking member, which may contact the medical device that is to be held by the arm and assist the arm in holding the medical device in place.

The shaft 250 of the second member 200 comprises a main body 252 extending from a proximal end 254 to a distal end 256. The main body 252 also has an upper surface 258, a lower surface 260, a first lateral side 262, and a second lateral side 264. The upper surface 258 is adjacent the first and second lateral sides 262, 264 and the lower surface 260 is adjacent the first and second lateral sides 262, 264.

In the illustrated embodiment, the shaft 250 is elongate and substantially box-shaped. Each of the upper surface 258, the lower surface 260, the first lateral side 262, and the second lateral side 264 is substantially rectangular in shape. The proximal end 254 of the shaft 250 is adjacent the arm 202 and the distal end 256 of the shaft 250 is adjacent the housing 270. Each of the first and second lateral sides 262, 264 define a first height $h_1$ extending from where the first and second lateral sides 262, 264 are adjacent the upper surface 258 to where the first and second lateral sides 262, 264 are adjacent the lower surface 260. Additionally, the upper surface 258 of the shaft 250 defines a first width $w_1{}^\star$. The first width $w_1{}^\star$ of the upper surface 258 of the shaft 250 of the second member 200 is greater than the first width $w_1$ of the upper surface 158 of the shaft 150 of the first member 100. A skilled artisan will be able to determine suitable shapes for the shaft and for each of the upper surface, lower surface, first lateral side, and second lateral side according to a particular example based on various considerations including the device the cross connector will engage and the location in the body at which the cross connector will be implanted. In other embodiments, one or more of the first lateral side, the second lateral side, the upper surface, and the lower surface may have any shape, including square, circular, elliptical, and triangular. Additionally, though the first lateral side and the second lateral side have the same size and shape in the illustrated embodiment, and the upper surface and the lower surface have the same size and shape, in alternative embodiments the first lateral side and upper surface may be shaped and sized differently than respectively, the second lateral side and the lower surface. Furthermore, the shaft may have any shape, including that of a rod, cone, and box. In other embodiments, the first width of the upper surface of the shaft of the second member may be substantially equal to, equal to, or greater by any amount than the first width of the upper surface of the shaft of the first member.

The proximal end 254 of the shaft 250 is disposed adjacent and in contact with the distal end 214 of the base 210 of the arm 202. The upper surface 258 is disposed on a plane that is substantially perpendicular to the plane (neither plane is illustrated in the Figures) on which the distal end 214 is disposed. Additionally, the proximal end 254 is integrally formed with the arm 202 and extends away from the proximal end 212 of the base 210; the distal end 256 is integrally formed with the housing 270, as well. A skilled artisan will be able to determine how to suitably configure the shaft with regard to the arm according to a particular example based on various considerations, including the device the cross connector will engage and the location in the body at which the cross connector will be implanted. In an alternative embodiment, the upper surface of the shaft may be disposed on a plane that is disposed at an angle to the plane on which the distal end of the base is disposed. In a different embodiment, the shaft may not be integrally formed with one or both of the arm and the housing, and instead may be attached to the arm, housing, or both via an adhesive or a mechanical attachment device. In other embodiments, the shaft may be attached to another portion of the arm, including one of the first or second lateral sides of the base and also may be attached to any portion of the housing.

The housing 270 is comprised of a main body 271, which includes a proximal side 272, a distal side 274 disposed opposite the proximal side 272, a first lateral side 276 disposed adjacent the proximal side 272 and the distal side 274, a second lateral side 278 disposed opposite the first lateral side 276 and adjacent the proximal side 272 and the distal side 274, an upper surface 280, and a lower surface 282. The main body 271 also defines a passageway 284, a channel 290, and a void 294.

The housing 270 is substantially box-shaped. As such, each of the proximal, distal, first lateral, and second lateral sides 272, 274, 276, 278 is substantially rectangular in shape. Additionally, the upper surface 280 is substantially square and the lower surface 282 is substantially square. Each of the upper surface 280 and the lower surface 282 defines an opening (described below). Any of the proximal, distal, first lateral, and second lateral sides 272, 274, 276, 278, and the upper and lower surfaces 280, 282 may have any shape, however. A skilled artisan will be able to determine how to suitably shape the housing and each of its components according to a particular example based on various considerations, including the size and shape of the first member and the location in the body at which the cross connector will be implanted. In an alternative embodiment, the housing may have any shape, including that of a pill, cone, cylinder, and cube. In a different embodiment, one or more of the proximal, distal, first lateral, and second lateral sides may have any shape, including square, triangular, elliptical, and circular. In another embodiment, one or both of the upper surface and the lower surface may have any shape, including square, triangular, elliptical, and circular.

The first and second lateral sides 276, 278 and the distal side 274 each have a second height $h_2$ extending from where the first and second lateral sides 276, 278 and the distal side 274 are adjacent the upper surface 280 to where the first and second lateral sides 276, 278 and the distal side 274 are adjacent the lower surface 282. The proximal side 272 has a third height $h_3$ extending from where the proximal side 272 is adjacent the upper surface 280 to where the proximal side 272 is adjacent the upper surface 258 of the shaft 250. As illustrated in FIG. 1, the second height $h_2$ is greater than the third height $h_3$ and the third height $h_3$ is greater than the first height $h_1$. A skilled artisan will be able to determine suitable first, second, and third heights according to a particular example based on various considerations, including the size and shape of the first member and the location in the body at which the cross connector will be implanted. In alternative embodiments, the first and second lateral sides of the shaft may have any height, the first and second lateral sides of the housing may have any height, and the proximal and distal sides of the housing may have any height. In another embodiment, the first height is equal to or greater than the second height. In a different embodiment, the second height is less than or equal to the third height.

In the illustrated embodiment, a passageway 284 extends from the proximal side 272 to the distal side 274 of the main body 271 of the housing 270. The proximal side 272 defines a first opening 285 that is semicircular in shape. The distal side 274 defines a second opening 286 that is also semicircular in shape. The first opening 285 and the second opening each define a fourth height $h_4$ and a second width $w_2$; the second opening 286 has substantially the same size and shape as the first opening 285, and, thus, the first and second openings 285, 286 have the same heights and widths. The passageway 284 also defines an inner surface 287. The fourth height $h_4$ is constant from the proximal side 272 to the distal side 274; the second width $w_2$ is constant from the proximal side 272 to the distal side 274, as well. In the illustrated embodiment, the fourth height $h_4$ is greater than the fifth height $h_5$ that is defined by the proximal end 154 of the shaft 150 of the first member 100. Additionally, the second width $w_2$ is greater than the first width $w_1$ of the upper surface 158 of the shaft 150 of the first member 100, but is less than the first width $w_1{}^\star$ of the upper surface 258 of the shaft 250 of the second member 200. This configuration is particularly advantageous because it allows for the shaft 150 of the first member 100 to be rotatably moved within the passageway 284 defined by the housing 270, pivotally moved within the passageway 284 defined by the housing 270, and slidably moved within the passageway 284 defined by the housing 270 (further described below). A skilled artisan will be able to determine suitable shapes for the first and second openings and the passageway, fourth and fifth heights, and a suitable first width of the upper surface of the shaft of the first member, first width of the upper surface of the shaft of the second member, and second width according to a particular example based on various considerations, including the size and shape of the first member and the location in the body at which the cross connector will be implanted. In other embodiments, one or both of the first and second openings may have any shape, including triangular, rectangular, elliptical, semi-elliptical, and circular; furthermore, the first opening may be shaped differently than the second opening. The first opening may also define a second width while the second opening defines a third width that is different than the second width in other embodiments. In different embodiments, the passageway may taper from the proximal side to the distal side, may taper from the distal side to the proximal side, or may taper from the proximal side to the midpoint of the passageway, then expand from the midpoint of the passageway to the distal side. In alternative embodiments, the second width may be equal to, substantially equal to, or greater than the first width of the upper surface of the shaft of the second member; the second width may be greater than the first width of the upper surface of the shaft of the first member by any amount in such embodiments, as well. In alternate embodiments, the fourth height may be substantially equal to the fifth height or be greater than the fifth height by any amount in other embodiments.

The main body 271 of the housing 270 also defines a channel 290; the channel 290 includes an upper opening 291, a lower opening 292, and an inner surface 293 and is in fluid communication with the passageway 284. The upper opening 291 is defined by the upper surface 280 of the housing and is substantially circular in shape. The lower opening 292 is defined by the inner surface 287 of the passageway 284. The lower opening 292 is substantially circular in shape. Each of the upper opening 291 and the lower opening 292 defines a first diameter $d_1$. The first diameter $d_1$ is constant from the upper opening 291 to the lower opening 292. The inner surface 293 of the channel 290 is threaded and configured to mate with a portion of the locking member 500 (described below). A skilled artisan will be able to determine suitable shapes and sizes for the upper and lower openings and the channel according to a particular example based on various considerations, including the size and shape of the first member and the shape and size of the locking member. In other embodiments, one or both of the upper and lower openings may have any shape, including rectangular, square, triangular, oval, and elliptical. In different embodiments, the channel may taper from the upper opening to the lower opening; it may also taper from the lower opening to the upper opening. The first diameter may have any suitable measurement in alternative embodiments, as well.

The main body 271 of the housing 270 also defines a void 294 which is defined by an upper opening 295 defined by the inner surface 297 of the main body 271 of the housing 270, a lower opening 296 defined by the lower surface 282 of the main body 271 of the housing 270, and an inner surface 297 that extends from the upper opening 295 to the lower opening 296. The void 294 is in fluid communication with the passageway 284. The upper opening 295 is substantially circular in shape and has a third diameter $d_3$. The lower opening 296 is also substantially circular in shape and has a second diameter $d_2$. As best illustrated in FIG. 4, the inner surface 297 that defines the void 294 tapers from the upper opening 295 to the lower opening 296; thus, the third diameter $d_3$ is greater than the second diameter $d_2$. The inner surface 297 is configured to mate with the saddle 300; more specifically, the inner surface 297 is formed such that it mates with the outer surface (described below) of the saddle 300 such that the saddle 300 is rotatably disposed within the void 294 and is in contact with the inner surface 297. A skilled artisan will be able to determine how to shape the upper opening, lower opening, and inner surface such that they define a suitable void and suitable second and third diameters according to a particular example based on various considerations, including the size and shape of the first member and the shape and size of the saddle. In other embodiments, one or both of the upper and lower openings may have any shape, including rectangular, square, triangular, oval, and elliptical. In different embodiments, the second and third diameters may be equal or the second diameter may be greater than the third diameter. In another embodiment, the main body may not define a lower opening; instead, the lower surface of the main body may be solid and the void may be partially defined by a base defined by the main body disposed above the lower surface of the main body. In such an embodiment, the inner surface and base may cooperatively define any height for the void.

The saddle 300 includes a main body 302 having an upper surface 304, a lower surface 306 substantially opposite the upper surface 304, and a side 308 extending from the upper surface 304 to the lower surface 306.

The side 308 is substantially smooth and defines first and second extensions 310, 312 that are disposed adjacent the upper surface 304. The smooth character of the side 308 allows for the saddle 300 to be easily rotated within the void 294. The first and second extensions 310, 312 extend opposite the lower surface 306 and each have a tip 320, 322, respectively. The first and second extensions 310, 312 help to define the shape of the upper surface 304. More specifically, the first and second extensions 310, 312 give the upper surface 304, generally, a u-shape when viewed from the side, as illustrated in FIG. 5. This u-shape is advantageous because it helps prevent excessive lateral movement of the shaft 150 of the first member 100, such as movement that will disrupt contact between the shaft 150 and the upper surface 304, when the shaft 150 is disposed within the saddle 300. In addition, the lower surface 306 is substantially circular in shape. A skilled artisan will be able determine a suitable saddle according to a particular example based on various considerations, including the size and shape of the void and the size and shape of the shaft of the first member. In another embodiment, the upper surface of the saddle may be parallel to the lower surface of the saddle. In different embodiments, the side may not define extensions or may define extensions that have any shape, including rectangular or rounded. In other embodiments, the lower surface of the saddle may have any shape, including square, rectangular, and triangular. Alternatively, the side of the saddle may not be smooth; rather, it may be threaded or include a mechanical attachment configured to engage the inner surface of the main body of the housing of the second member.

As best illustrated in FIG. 5, the upper surface 304 has a fourth diameter $d_4$ extending from the first tip 320 to the second tip 322. The lower surface defines a fifth diameter $d_5$; the fourth diameter $d_4$ is greater than the fifth diameter $d_5$. As such, the saddle 300 is tapered from the upper surface 304 to the lower surface 306. In addition, the fourth diameter $d_4$ is less than the third diameter $d_3$ and the fifth diameter $d_5$ is less than the second diameter $d_2$. A skilled artisan will be able to determine suitable second, third, fourth, and fifth diameters according to a particular example based on various considerations, including the size and shape of the void and the size and shape of the shaft of the first member. In other embodiments, the fourth diameter may be equal to or less than the fifth diameter. In alternative embodiments, the saddle may taper from the lower surface to the upper surface.

The saddle 300 is configured to be housed in the void 294 defined by the main body 271 of the housing 270. The side 308 is complementary to the inner surface 297 of the main body 271 and is sized and shaped, as described above, such that it maintains its position within the housing 270 and does not escape through the lower opening 296 defined by the lower surface 282. The shape of the saddle 300 and the inner surface 297 of the void are sufficient to maintain the saddle 300 within the housing 270. The use of an adhesive or mechanical attachment mechanism is not required. A skilled artisan will be able to determine how to suitably size and shape the saddle and how to suitably ensure that it maintains its position within the void according to a particular example based on various considerations, including the shape and size of the void and the material of which the saddle is comprised. In other embodiments, the saddle may be comprised of a material that expands once it is placed in the void in order to maintain the position of the saddle within the void. In different embodiments, the saddle may be mechanically or adhesively attached to the inner surface that defines the void.

FIG. 5A illustrates an alternative saddle 300' that includes a flange 330'. The saddle 300' includes a main body 302' having an upper surface 304', a lower surface 306' substantially opposite the upper surface 304', and a side 308' extending from the upper surface 304' to the lower surface 306'. In the illustrated embodiment, the flange 330' is disposed on and extends circumferentially along the side 308'. The flange 330' is configured to mate with a cavity defined by the inner surface of the passageway of the main body (not illustrated in the Figures) by extending into said cavity. The flange 330' may be comprised of the same material as the saddle 300' or a different material. The flange 330' provides an extra mechanism for ensuring that the saddle 300' stays housed within the void (not illustrated in the Figures). A skilled artisan will be able to determine how to suitably shape and size the flange according to a particular example based on various considerations, including the shape and size of the void and the size of the saddle. In another embodiment, the flange may have any shape, including square, rectangular, and triangular, and may or may not extend around the entirety of the saddle. In different embodiments, the saddle may include two or more flanges.

The stop member 400 comprises an upper surface 402, a lower surface 404, and a side 406 extending from the upper surface to the lower surface 404. In the illustrated embodiment, the stop member 400 is cylindrical in shape. Thus, each of the upper surface 402 and the lower surface 404 is circular in shape. The upper surface 402 has the same diameter (not illustrated in the Figures) as the lower surface 404. Additionally, the side 406 has a sixth height $h_6$, which is greater than the fifth height $h_5$ of the channel 162 defined by the shaft 150 of the first member 100. The sixth height $h_6$ is greater than the fifth height $h_5$ so that the stop member 400 may prevent the proximal end 154 of the shaft 150 of the first member 100 from sliding too greatly retracted into the passageway 284 by contacting the proximal side 272 of the housing 270. A skilled artisan will be able to determine how to suitably shape and size the stop member according to a particular example based on various considerations, including the size and shape of the channel defined by the shaft of the first member and the size and shape of the upper surface of the channel of the second member. In another embodiment, the stop member may have any shape, including pill, pyramid, cube, and box. In alternative embodiments, the upper and lower surface may have any shape, including triangular, rectangular, elliptical, square. Additionally, in other embodiments, the upper surface may have a diameter that is greater than, less than, substantially equal to, or equal to the diameter of the lower surface.

The upper surface 402 of the stop member 400 includes an indented portion 408 and the side 406 of the stop member 400 includes a threaded portion 410. The indented portion 408 extends from the upper surface 402 towards the lower surface 404 and is configured to allow a driver or other instrument (not illustrated in the Figures) to be inserted into the indented portion 408. Once an instrument, such as a driver, is inserted into the indented portion 408 and engages the stop member 400, rotational movement of the driver rotates the stop member 400. This rotational movement advances the stop member 400 toward the lower opening 166 of the channel 162. This is accomplished through the threaded portion 410 of the stop member 400 mating with the inner surface 168 of the channel 160 of the shaft 150 of the first member 100. The stop member 400 is advanced such that its lower surface 404 is in contact with the upper surface 258 of the shaft 250 of the second member 200. A skilled artisan will be able to determine how to suitably advance the stop member within the channel of the shaft of the first member according to a particular example based on various considerations, including the size and shape of the channel defined by the shaft of the first member and the size and shape of the upper surface of the channel of the second member. In other embodiments, the stop member may be advanced through a tapering channel. In a different embodiment, the stop member may be permanently disposed in a single position within the channel. Alternatively, the stop member may be advanced from the lower opening of the channel toward the upper opening, in other embodiments.

Figure 2:
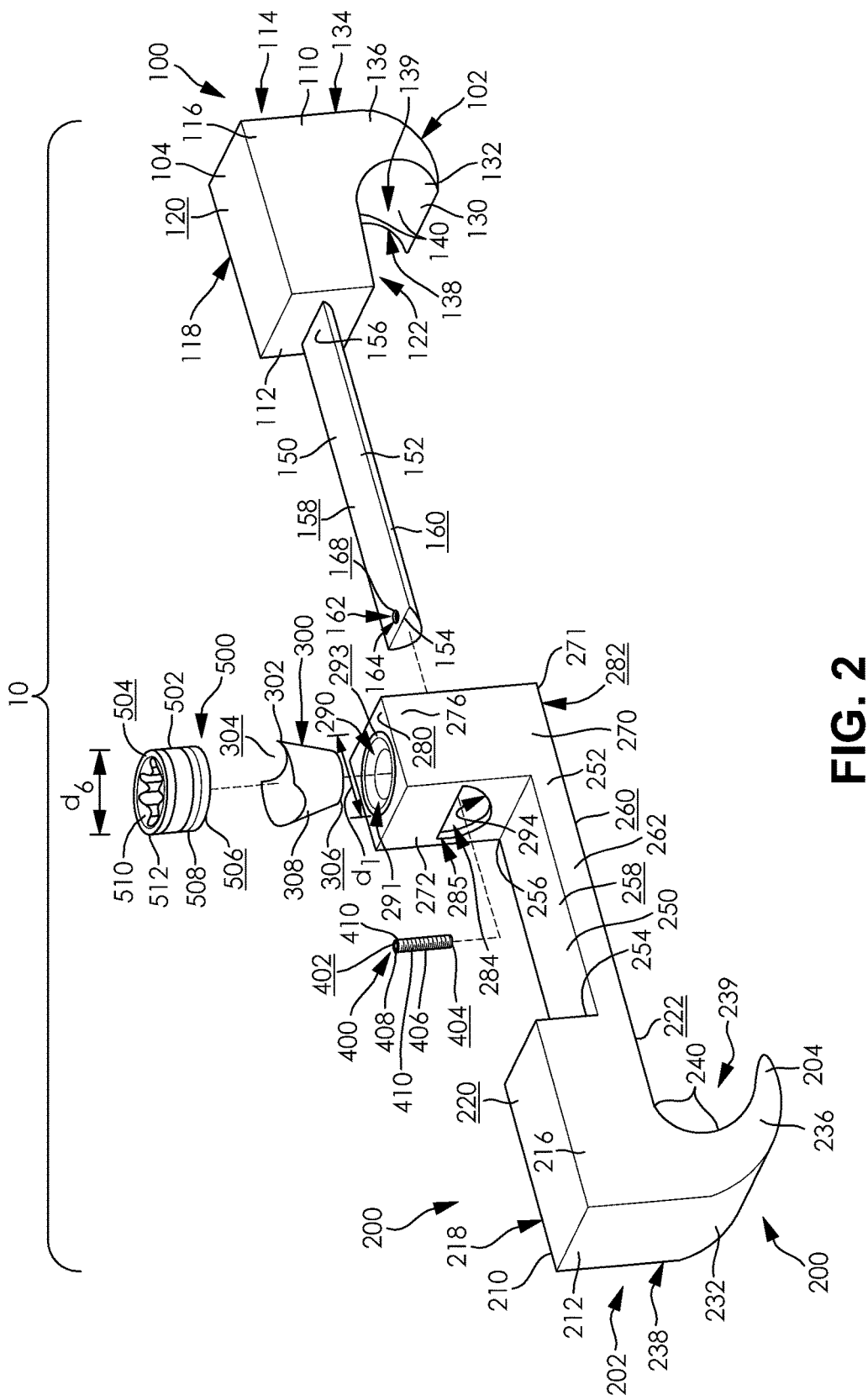
FIG. 2 is an exploded view of the cross connector illustrated in FIG. 1.
Figure 6:
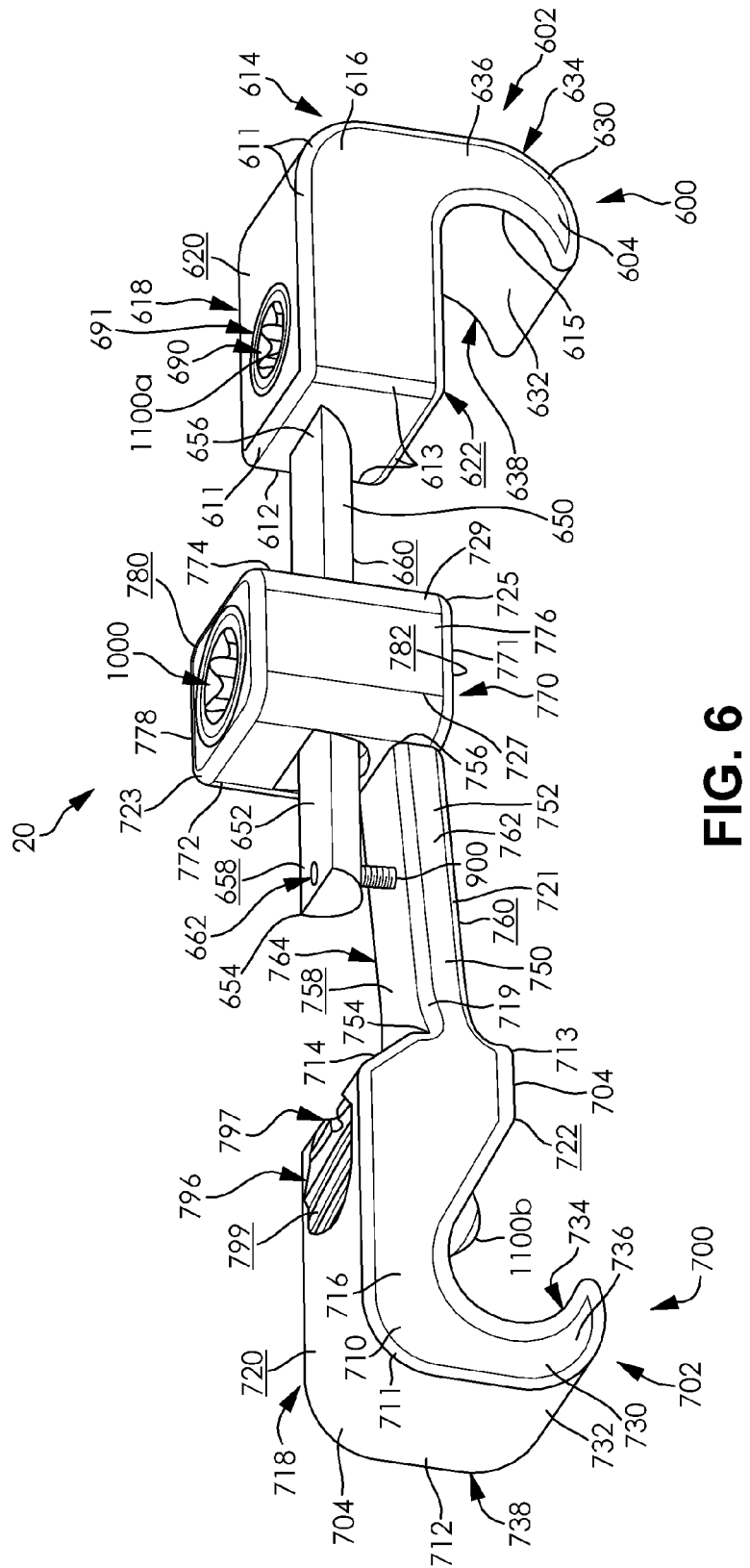
FIG. 6 is a perspective view of another example cross connector.

FIGS. 2 and 4 best illustrate the locking member 500. The locking member 500 includes a main body 502, an upper surface 504, a lower surface 506 disposed opposite the upper surface 504, and a side 508 extending from the upper surface 504 to the lower surface 506. The locking member 500 is rotatably disposed within the channel 290 of the housing 270 of the second member 200.

Each of the upper surface 504 and the lower surface 506 is substantially circular in shape and has a sixth diameter $d_6$. The side 508 is parallel to each of the upper and lower surfaces 504, 506 and is threaded. As such, the main body 502 is substantially cylindrical in shape. The upper surface 504 contains an indented portion 510 that is configured to mate with a driver or other instrument. Once a driver or other instrument has mated with the indented portion 510, rotational movement of the driver and, thus, the locking member 500, advances the locking member 500 within the channel 290 towards the passageway 284. The threaded portion 512 of the side 508 is configured to mate with the threaded inner surface 293 of the channel 290 and is the mechanism by which the locking member 500 advances. Advancement of the locking member 500 ultimately results in contact between the lower surface 506 and the shaft 150 of the first member 100. The locking member 500 is configured such that when its lower surface 506 is in contact with the shaft 150 of the first member 100, it engages the shaft 150 and prevents the shaft 150 from sliding, rotating, and pivoting within the housing 270. A skilled artisan will be able to determine a suitable locking member to use in conjunction with the housing and the first member according to a particular example based on various considerations, including the size and shape of the channel. In other embodiments, the locking member may attach to the shaft of the first member via a mechanical attachment and prevent movement of the shaft within the housing through use of the mechanical attachment. In another embodiment, the lower surface of the locking member may be coated with an adhesive and prevent movement of the shaft of the first member through use of the adhesive. Alternatively, the locking member may taper or expand from the upper surface to the lower surface and the upper surface may have a different diameter than the lower surface.

In use, and described in greater detail below, the main body 152 of the shaft 150 of the first member 100 is captively disposed within the passageway 284 of the housing 270 of the second member 200 and is in contact with the upper surface 304 of the saddle 300. In addition, the proximal end 154 of the shaft 150 is disposed above the main body 252 of the shaft 250 of the second member 200. The shaft 150 of the first member 100 may be moved within the housing 270 when a rotational, pivotal, or sliding force is applied to the first member 100.

Arrow AA indicates a sliding force being applied to the first member 100. Such a sliding force AA moves the first member 100 along a plane (not illustrated in the Figures) on which the upper surface 154 of the shaft 150 is disposed. The sliding force AA may be applied either to the base 110 or the shaft 150 of the first member 100 and may move the proximal end 154 of the shaft 150 towards or away from the base 210 of the second member 200. The shaft 150 may be slid such that its proximal end 154 is adjacent the base 210 of the second member 200, such that its proximal end 154 is adjacent the proximal side 272 of the housing 270, and such that the proximal end 154 of the shaft 150 is disposed at any point therebetween.

Arrow BB indicates a pivoting force being applied to the first member 100. Such a pivoting force BB moves the first member 100 such that the main body 152 of the shaft 150 may contact the inner surface 287 adjacent each of the first and second openings 285, 286. The pivoting force BB moves the shaft 150 such that the shaft 150, at its maximally pivoted positions, contacts a portion of the inner surface 287 adjacent the first opening 285 that is directly opposite a corresponding portion of the inner surface 287 adjacent the second opening 286. Thus, when the first member 100 has been pivotally moved as far as is possible in either direction indicated by Arrow BB, a portion of the main body 152 of the shaft 150 will contact a portion of the inner surface 287 adjacent the first opening 285 and a portion of the inner surface 287 adjacent the second opening 286. This pivoting movement is guided by the upper surface 304 of the saddle 300, which is rotatable within the housing 270 as described above. The upper surface 304 is in contact with the shaft 150 and displaces the shaft 150 in either direction.

Additionally, as is described above, the first width $w_1$ of the upper surface 154 of the shaft 150 of the first member 100 is less than the first width $w_1^*$ of the upper surface 258 of the shaft 250 of the second member 200. In the illustrated embodiment, the first width $w_1^*$ of the upper surface 258 of the shaft 250 of the second member 200 is great enough that, when the shaft 150 of the first member 100 is maximally pivoted in either direction, the proximal end 154 of the shaft 150 is still disposed over the upper surface 258 of the shaft 250 of the second member 250. This configuration is advantageous because it prevents the stop member 400 from engaging either of the first and second lateral sides 262, 264 of the shaft 250, which could result in the first member 100 becoming unable to continue to pivot. This configuration also ensures that the stop member 400 stays in contact with the shaft 250 of the second member 200.

Arrow CC indicates a rotating force being applied to the first member 100. Such a rotating force CC moves the entire first member 100 such that it is rotated about the longitudinal axis (not illustrated in the Figures) of the shaft 150 of the first member 100. The rotating force CC allows the upper surface 158 of the shaft 150, at its first maximally rotated position, to be adjacent the first extension 310 and angled relative to the first extension 310 of the saddle 300 when rotating force CC is applied in a first direction. The rotating force CC also allows the upper surface 158 of the shaft 150, at its second maximally rotated position, to be adjacent the second extension 312 and angled relative to the second extension 312 of the saddle 300 when rotating force CC is applied in a second direction that is opposite the first direction.

The locking member 500 contacts the shaft 150 of the first member 100 and locks the first member 100 in place once desired sliding, pivoting, and rotating alignments have been achieved. Specifically, the lower surface 506 of the locking member 500 locks the shaft 150 in place, which in turn stabilizes the entire first member 100. In the illustrated embodiment, as it pertains to rotational movement, the locking member 500 can engage the shaft 150 in two predetermined positions: when the upper surface 158 of the shaft 150 is disposed at a first angle (not illustrated in the Figures) relative to the plane containing the upper surface 280 of the housing 270 and at a second angle (not illustrated in the Figures) relative to the plane containing the upper surface 280 of the housing 270. Thus, shaft 150 may be considered binary in regards to its rotational configurations. The locking member 500, however, may engage the shaft 150 in any pivoted configuration described above and at any sliding configuration described above. A skilled artisan will be able to determine how to suitably engage the locking member with the shaft to lock it into pivotal, slidable, and rotational alignments according to a particular example based on various considerations, including the size and shape of the shaft and where the cross connector will be implanted within the body. In an alternative embodiment, the locking member may engage the shaft of the first member in any rotated configuration; in such an embodiment, the cross connector is not rotationally binary. In another configuration, the proximal end of the first member may slide over the base of the second member. In a different configuration, the first and second openings defined by the proximal and distal sides of the housing may be larger or smaller and, thus, change the angles and dimensions that the shaft may pivot in relation to the housing. In other embodiments, the shaft may only pivot, rotate, or slide within the housing. In alternative embodiments, the shaft may only pivot and slide, rotate and slide, or pivot and rotate within the housing.

Each of FIGS. 6, 7, 8, and 9 illustrates another example cross connector 20 or a component thereof. The illustrated cross connector 20 is similar to the cross connector 10 illustrated in FIGS. 1, 2, 3, 4, and 5 and described above, except as described below. Thus, the cross connector 20 includes a first member 600, a second member 700, a saddle 800, a stop member 900, a locking member 1000, and first and second set screws 1100a, 1100b.

In the illustrated embodiment, each of the first and second set screws 1100a, 1100b have proximal ends 1102a, 1102b, distal ends 1104a, 1104b, sides 1106a, 1106b that are threaded, and indented portions 1108a, 1108b configured to engage a driver or other similar device. The sides 1106a, 1106b partially taper from the proximal ends 1102a, 1102b to the distal ends 1104a, 1104b. The set screws 1100a, 1100b are configured to mate with the channels (described below) defined by the first and second members 600, 700 and to engage rods or other medical devices (not illustrated in the Figures) that are engaged by the first and second members 600, 700, respectively. A skilled artisan will be able to determine how to suitably size and shape the first and second set screws according to a particular example based on various considerations, including the sizes and shapes of the channels defined by the first and second members. In other embodiments, a nut, a bolt, a screw, or any other mechanical device may be used in place of a set screw. In a different embodiment, the distal ends of the set screws may be coated with adhesives in order to more firmly engage the rods or other medical devices.

The first member 600 comprises an arm 602 and a shaft 650. The arm 602 is comprised of a main body 604 having a base 610 and a grip 630. The base 610 includes proximal side 612, a distal side 614 opposite the proximal side 612, a first lateral side 616, a second lateral side 618 opposite the first lateral side 616, an upper surface 620, and a lower surface 622. The grip 630 is integrally formed with the base 610 and comprises a proximal side 632, a distal side 634 opposite the proximal side 632, a first lateral side 636, and a second lateral side 638 disposed opposite the first lateral side 636. The shaft 650 of the first member 600 comprises a main body 652 extending from a proximal end 654 to a distal end 656. The main body 652 has an upper surface 658 and a lower surface 660 and defines a channel 662 extending from the upper surface 658 to the lower surface 660.

In the illustrated embodiment, the first member 600 includes a first rounded portion 611 disposed adjacent the upper surface 620 of the base 610 and adjacent each of the proximal side 612, the distal side 614, the first lateral side 616, and the second lateral side 618. The first member 600 also includes a second rounded portion 613 disposed adjacent the proximal side 612, the lower surface 622, the first lateral side 616, and the second lateral side 618. In addition, the first member 600 includes a third rounded portion 615 disposed adjacent the first lateral side 616 of the base 610, and the first lateral side 636, the proximal side 632, and the distal side 634 of the grip 630. Furthermore, the first member 600 includes a fourth rounded portion (not illustrated in the Figures) disposed adjacent the second lateral side 618 of the base 610, and the second lateral side 638, the proximal side 632, and the distal side 634 of the grip 630. A skilled artisan will be able to determine whether to include one or more of the first, second, third, and fourth rounded portions and how to suitably configure the dimensions of said rounded portions according to a particular example based on various considerations, including the size and shape of the second member and the size and shape of the shaft of the first member. In other embodiments, the first member may include any combination of the first, second, third, and fourth rounded portions. In other embodiments, five, six, seven, or more than seven rounded portions may be included.

The first member 600 also defines a first arm channel 690 extending from the upper surface 620 to the lower surface 622 of the base 610 of the second member 600. The first arm channel 690 includes a first opening 691 defined by the upper surface 620 that is circular, a second opening 692 defined by the lower surface 622 that is circular, and an inner surface 693 extending from the first opening 691 to the second opening 692. As best illustrated in FIG. 8, the inner surface 693 is threaded and is configured to engage the side 1106*a* of the first set screw 1100*a*. Each of the first opening 691 and the second opening 692 has the same diameter; further, the diameter of the first arm channel 690 is constant from the first opening 691 to the second opening 692. The set screw 1100*a* may be advanced toward the second opening 692 via rotational force on the proximal end 1102*a* of the set screw 1100*a*. A skilled artisan will be able to determine suitable sizes, shapes, and diameters of the first and second openings and the first arm channel according to a particular example based on various considerations, including the size and shape of the set screw and the rod or other medical device that the set screw will engage. In other embodiments, the first arm channel may taper or expand from the first opening to the second opening. In other embodiments, each of the first and second openings may have any shape, including rectangular, square, triangular, and elliptical.

Additionally, the first arm channel 690 includes a central axis 694 that is disposed at a first angle $\alpha_1$ relative to the plane 695 containing the upper surface 658 of the shaft 650 of the first member 600. A skilled artisan will be able to determine a suitable first angle according to a particular example based on various considerations, including the size and shape of the set screw and the rod or other medical device that the set screw will engage. Examples of suitable first angles include angles between about 70° and about 110°, angles between about 80° and about 100°, and angles between about 85° and about 95°.

The second member 700 comprises an arm 702, a shaft 750, and a housing 770. The arm 702 is comprised of a main body 704 having a base 710 and a grip 730. The base 710 includes proximal side 712, a distal side 714 opposite the proximal side 712, a first lateral side 716, a second lateral side 718 opposite the first lateral side 716, an upper surface 720, and a lower surface 722. The grip 730 comprises a proximal side 732, a distal side 734 opposite the proximal side 732, a first lateral side 736, and a second lateral side 738 disposed opposite the first lateral side 736. The shaft 750 of the second member 700 comprises a main body 752 extending from a proximal end 754 to a distal end 756. The main body 752 also has an upper surface 758, a lower surface 760, a first lateral side 762, and a second lateral side 764. The housing 770 is comprised of a main body 771, which includes a proximal side 772, a distal side 774 disposed opposite the proximal side 772, a first lateral side 776 disposed adjacent the proximal side 772 and the distal side 774, a second lateral side 778 disposed opposite the first lateral side 776 and adjacent the proximal side 772 and the distal side 774, an upper surface 780, and a lower surface 782. The main body 771 also defines a passageway 784, a channel 790, and a void 794.

In the illustrated embodiment, the second member 700 includes a first rounded portion 711 disposed adjacent the upper surface 720, the proximal side 712, and the first lateral side 716 of the base 710 and adjacent the proximal side 732 and the first lateral side 736 of the grip 730. The second member 700 also includes a second rounded portion 713 disposed adjacent the distal side 714, the lower surface 722, and the first lateral side 714 of the base 710 and the first lateral side 736 and the distal side 734 of the grip 730. In addition, the second member 700 includes a third rounded portion (not illustrated in the Figures) disposed adjacent the upper surface 720, the proximal side 712, and the second lateral side 718 of the base 710 and adjacent the proximal side 732 and the second lateral side 738 of the grip 730. The second member 700 also includes a fourth rounded portion (not illustrated in the Figures) disposed adjacent the distal side 714, the lower surface 722, and the second lateral side 716 of the base 710 and the second lateral side 738 and the distal side 734 of the grip 730. The second member 700 further includes a fifth rounded portion 719 disposed adjacent the upper surface 758 of the shaft 750 and the first and second lateral sides 762, 764 of the shaft 750. The fifth rounded portion 719 is particularly advantageous because it allows for the stop member 900 to be easily and quickly returned to a position in which the stop member 900 is disposed over the upper surface 758 of the shaft 750 if the stop member 900 is pivoted such that it extends past the boundaries of the upper surface 758 of the shaft. The second member 700 further includes a sixth rounded portion 721 disposed adjacent the lower surface 760 of the shaft 750 and the first and second lateral sides 762, 764 of the shaft 750. The second member 700 additionally includes a seventh rounded portion 723 disposed adjacent the upper surface 780 of the housing 770 and the proximal, distal, first lateral, and second lateral sides 772, 774, 776, 778 of the housing 770. In addition, the second member 700 includes an eighth rounded portion 725 disposed adjacent the lower surface 782 of the housing 770 and the proximal, distal, first lateral, and second lateral sides 772, 774, 776, 778 of the housing 770. The second member 700, furthermore, includes ninth and tenth rounded portions 727, 729 and eleventh and twelfth rounded portions (not illustrated in the Figures). The ninth rounded portion 727 is disposed adjacent each of the proximal side 772 and the first lateral side 776 of the housing 770; the tenth rounded portion 729 is disposed adjacent each of the distal side 774 and the first lateral side 776 of the housing 770. The eleventh rounded portion is disposed adjacent each of the proximal side 772 and the second lateral side 778 of the housing 770; the twelfth rounded portion is disposed adjacent each of the distal side 774 and the second lateral side 778 of the housing 770. A skilled artisan will be able to determine whether to include one or more of the first, second, third, fourth, fifth, sixth, seventh, eighth, ninth, tenth, eleventh, and twelfth rounded portions and how to suitably configure the dimensions of said rounded portions according to a particular example based on various considerations, including where the cross connector will be implanted within the body and the size and shape of the shaft of the first member. In other embodiments, the first member may include any combination of the first, second, third, fourth, fifth, sixth, seventh, eighth, ninth, tenth, eleventh, and twelfth rounded portions. In other embodiments, thirteen, fourteen, fifteen, or more than fifteen rounded portions may be included.

The second member 700 also defines a second arm channel 796 extending from the upper surface 720 to the lower surface 722 of the base 710 of the second member 700. The second arm channel 796 includes a first opening 797 defined by the upper surface 720 that is circular, a second opening 798 defined by the lower surface 722 that is circular, and an inner surface 799 extending from the first opening 797 to the second opening 798. As best illustrated in FIG. 8, the inner surface 799 is threaded and is configured to engage the side 1106b of the second set screw 1100b. Each of the first opening 797 and the second opening 798 has the same diameter; further, the diameter of the second arm channel 796 is constant from the first opening 797 to the second opening 798. The set screw 1100b may be advanced toward the second opening 798 via rotational force on the proximal end 1102b of the set screw 1100b. A skilled artisan will be able to determine suitable sizes, shapes, and diameters of the first and second openings and the second arm channel according to a particular example based on various considerations, including the size and shape of the set screw and the rod or other medical device that the set screw will engage. In other embodiments, the second arm channel may taper or expand from the first opening to the second opening. In other embodiments, each of the first and second openings may have any shape, including rectangular, square, triangular, and elliptical.

Additionally, the second arm channel 796 includes a central axis 795 that is disposed at a second angle $\alpha_2$ relative to the plane 695 containing the upper surface 658 of the shaft 650 of the first member 600. In the illustrated embodiment, the second angle $\alpha_2$ is greater than the first angle $\alpha_1$. A skilled artisan will be able to determine a suitable second angle according to a particular example based on various considerations, including the size and shape of the set screw and the rod or other medical device that the set screw will engage. Examples of suitable second angles include angles between about 90° and about 130°, angles between about 100° and about 120°, and angles between about 105° and about 115°. Additionally, in other embodiments the second angle may be greater than, equal to, about equal to, or less than the first angle.

Figure 9:
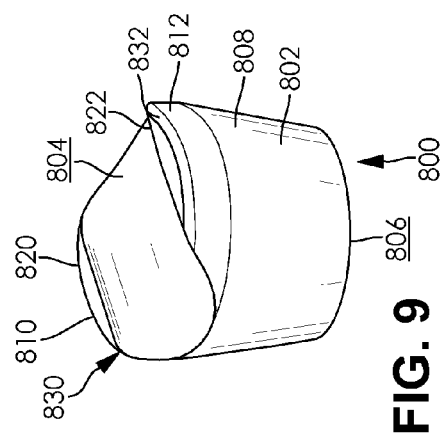
FIG. 9 is a magnified perspective view of the saddle illustrated in FIG. 8.
Figure 10:
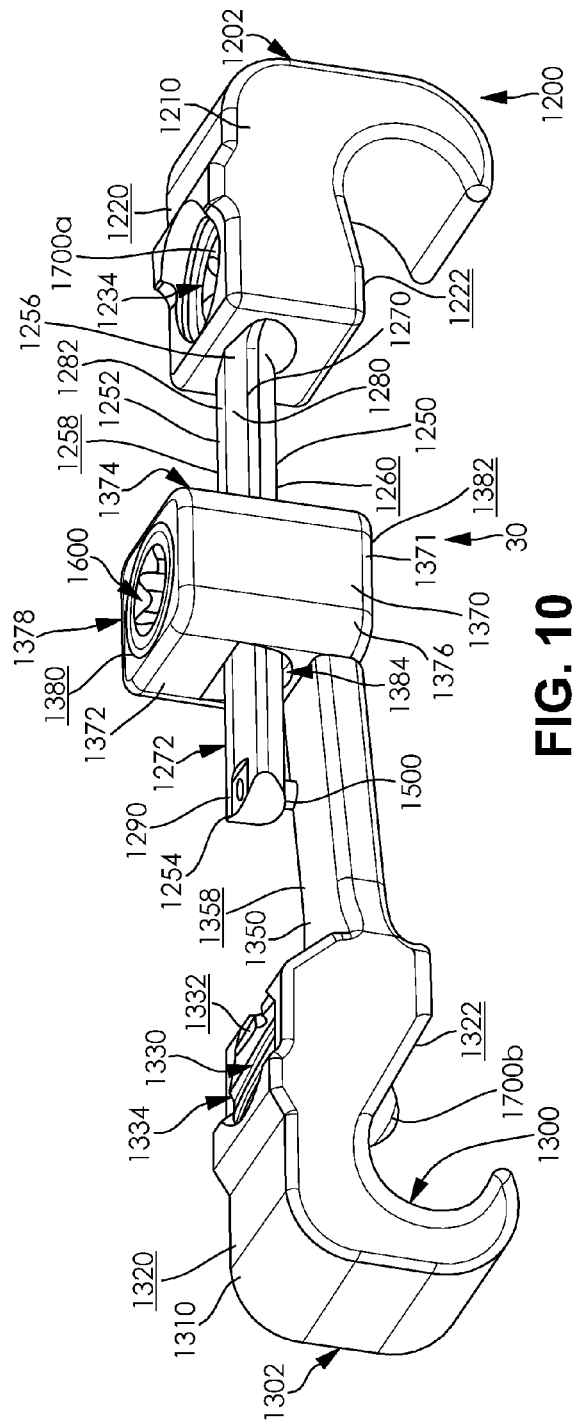
FIG. 10 is a perspective view of another example cross connector.
Figure 11:
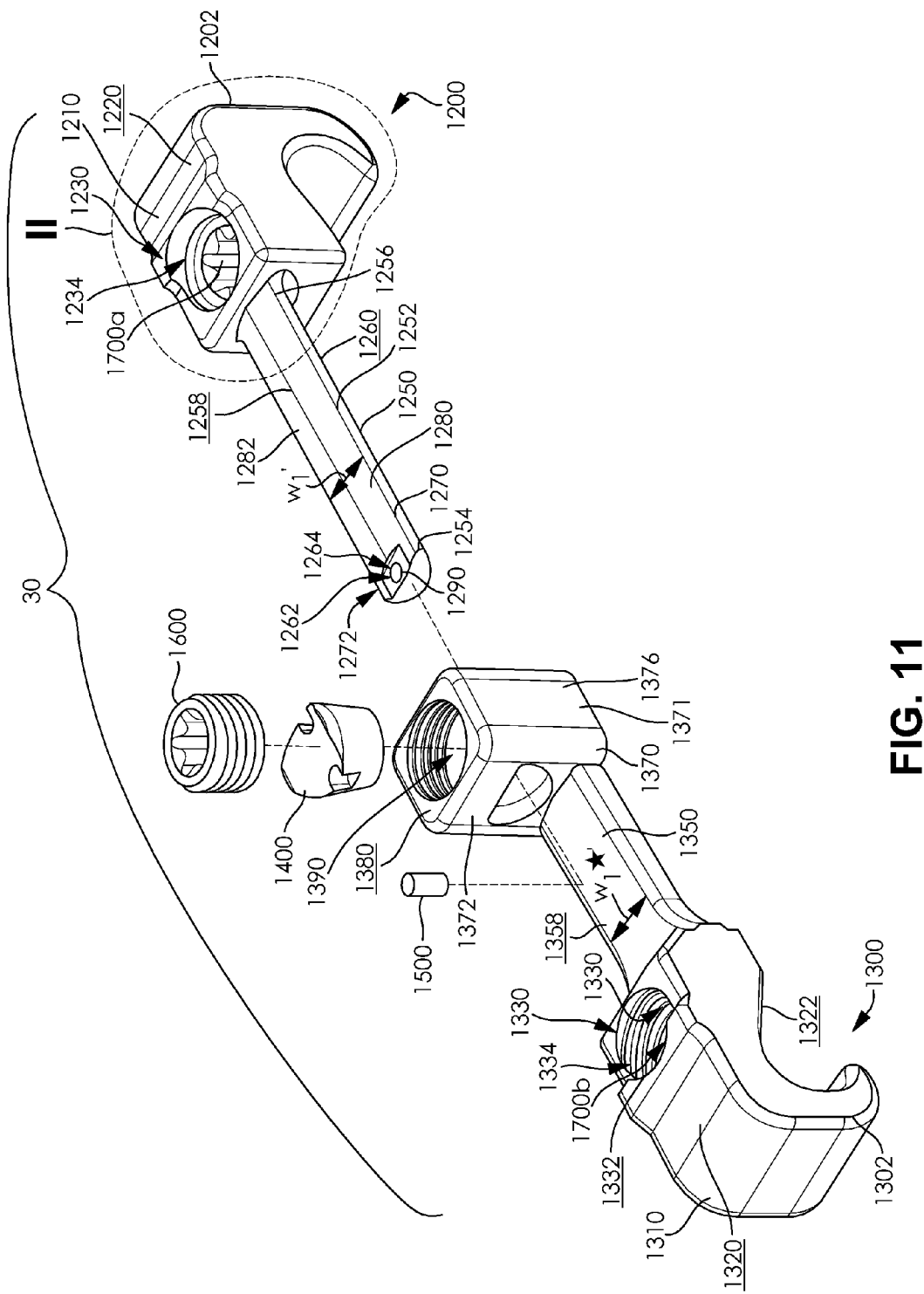
FIG. 11 is an exploded view of the cross connector illustrated in FIG. 10.

FIG. 9 best illustrates the saddle 800. The saddle 800 includes a main body 802 having an upper surface 804, a lower surface 806 substantially opposite the upper surface 804, a side 808 extending from the upper surface 804 to the lower surface 806, a first extension 810, and a second extension 812.

In the illustrated embodiment, the first and second extensions 810, 812 form first and second platforms 820, 822, rather that first and second tips, as are present in saddle 800. The first and second platforms 820, 822 are disposed on a plane (not illustrated in the Figures) that is substantially parallel to the plane containing the lower surface 806. Furthermore, the first platform 820 and the side 808 cooperatively define a first rounded portion 830 disposed adjacent the first platform 820 and the side 808. The second platform 822 and the side 808 cooperatively define a second rounded portion 832 disposed adjacent the second platform 822 and the side 808. A skilled artisan will be able to determine whether to include first and second platforms and how to suitably size and shape said platforms according to a particular example based on various considerations, including the size and shape of the shaft of the first member and the size and shape of the passageway of the housing of the second member. In other embodiments, the saddle may include only one, three, or greater than three platforms. In different embodiments, one or more of the first and second platforms may be disposed on a plane that is set at an angle relative to the plane containing the lower surface of the saddle. In alternative embodiments, the saddle does not have first and second rounded portions.

Each of FIGS. 10, 11, 12, 13, 13A, 14, 15, 16, 17, 18, and 19 illustrates another example cross connector 30 or a component thereof. The illustrated cross connector 30 is similar to the cross connector 20 illustrated in FIGS. 6, 7, 8, and 9 and described above, except as described below. Thus, the cross connector 30 includes a first member 1200, a second member 1300, a saddle 1400, a stop member 1500, a locking member 1600, and first and second set screws 1700a, 1700b.

In the illustrated embodiment, the first member 1200 comprises an arm 1202 and a shaft 1250. The second member 1300 comprises an arm 1302, a shaft 1350, and a housing 1370.

The shaft 1250 of the first member 1200 comprises a main body 1252 extending from a proximal end 1254 to a distal end 1256. The main body 1252 has an upper surface 1258 and a lower surface 1260 and defines a channel 1262 extending from the upper surface 1258 to the lower surface 1260. The main body 1252 also defines a first rounded portion 1270 disposed adjacent the upper and lower surfaces 1258, 1260 and a second rounded portion 1272 disposed adjacent the upper and lower surfaces 1258, 1260. The upper surface 1258 of the shaft 1250 defines a first width $w_1'$.

The upper surface 1258 is faceted. Thus, the upper surface 1258 includes a first portion 1280 and a second portion 1282. The first portion 1280 is adjacent each of the second portion 1282 and the first rounded portion 1270 and the second portion 1282 is adjacent each of the first portion 1280 and the second rounded portion 1272. In the illustrated embodiment, the first and second portions 1280, 1282 are faceted to the same degree and the faceting extends from the distal end 1256 of the main body 1252 to the indented portion (described below) of the main body 1252. A skilled artisan will be able to determine whether the upper surface should be faceted and to what degree to facet the upper surface according to a particular example based on various considerations, including the size and shape of the housing of the second member. In other embodiments, the upper surface is not faceted. In different embodiments, the first portion is faceted to a different degree than the second portion. In alternative embodiments, only a portion of the upper surface of the shaft is faceted. Alternatively, the shaft may not include first and second rounded portions and one or both of the first and second portions may be directly adjacent the lower surface.

The upper surface 1258 also includes an indented portion 1290 disposed adjacent the upper opening 1264 of the channel 1262. The indented portion 1290 is disposed adjacent the proximal end 1254 of the main body 1252 and extends towards the distal end 1256 of the main body 1256. In the illustrated embodiment, the indented portion 1290 surrounds the upper opening 1264 and is cooperatively defined by the first and second portions 1280, 1282. The indented portion 1290, however, does not fully extend to either of the first or second rounded portions 1270, 1272. A skilled artisan will be able to determine whether to include an indented portion and how to suitably configure the indented portion according to a particular example based on various considerations, including the shape and size of the locking member and the shape and size of the shaft of the first member. The indented portion may have any depth relative to the lower surface of the shaft of the first member. Additionally, in other embodiments, the indented portion may fully extend to the distal end of the shaft of the first member, or may extend any portion of the way to the distal end. In different embodiments, the indented portion may be fully defined by only one of the first or second portions of the shaft. In alternative embodiments, the indented portion may only partially surround the upper opening of the channel. In other embodiments, the upper surface may not define an indented portion.

Figure 17:
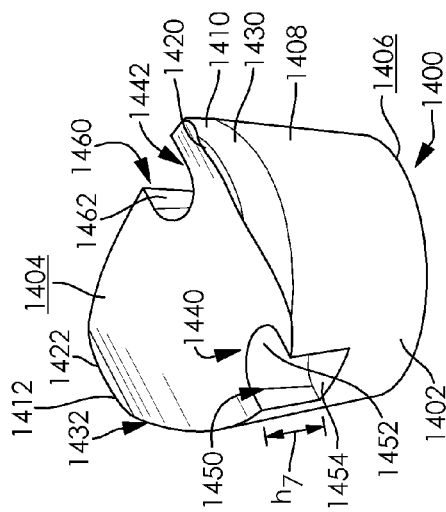
FIG. 17 is a magnified perspective view of the saddle illustrated in FIG. 11.

FIG. 17 best illustrates the saddle 1400. The saddle 1400 is similar to the saddle 800 described above, except as described below. Thus, the saddle 1400 includes a main body 1402 having an upper surface 1404, a lower surface 1406 substantially opposite the upper surface 1404, a side 1408 extending from the upper surface 1404 to the lower surface 1406, a first extension 1410, a second extension 1412, a first platform 1420, a second platform 1422, a first rounded portion 1430, and a second rounded portion 1432.

The side 1408 tapers from the upper surface 1404 to the lower surface 1406 and is configured to be held captive in the void of the housing of the second member (described in greater detail below).

In the illustrated embodiment, the upper surface 1404 and the side 1408 cooperatively define first and second cavities 1440, 1442. The first cavity 1440 defines an opening 1450, a side 1452, a base 1454, and a seventh height $h_7$ extending from the base 1454 to the opening 1450. The side 1452 is c-shaped and the cavity 1440 is configured to engage the stop member 1500, described in greater detail below. The opening 1450 is cooperatively defined by the upper surface 1404 and the side 1452 of the first cavity 1440.

The second cavity 1442 defines an opening 1460, a side 1462, a base (not illustrated in the Figures), and an eighth height (not illustrated in the Figures) extending from the base to the opening 1460. The side 1462 is c-shaped and the cavity 1442 is configured to engage the stop member 1500, described in greater detail below. The opening 1460 is cooperatively defined by the upper surface 1404 and the side 1462 of the second cavity 1442. The second cavity 1442 is disposed substantially opposite the first cavity 1440 relative to the longitudinal axis (not illustrated in the Figures) of the saddle 1400. Additionally, the eighth height is substantially equal to the seventh height $h_7$.

A skilled artisan will be able to determine whether to include one or more cavities and how best to size and shape the first and second cavities according to a particular example based on various considerations, including the size and shape of the stop member and the size and shape of the housing of the second member. In other embodiments, the saddle may include zero, one, three, or more than three cavities. In different embodiments, the seventh height may be greater than, less than, equal to, or substantially equal to the eighth height. In alternative embodiments, one or both of the first and second cavities may have any shape, including circular, square, triangular, and semi-circular. The first cavity may have the same shape as the second cavity; it may also have a different shape than the second cavity.

The housing 1370 is similar to the housing 770 described above, except as described below. Thus, the housing is comprised of a main body 1371, which includes a proximal side 1372, a distal side 1374, a first lateral side 1376, a second lateral side 1378, an upper surface 1380, and a lower surface 1382. The main body 1371 also defines a passageway 1384, a channel 1390, and a void 1394.

In the illustrated embodiment, the passageway 1384 includes a first portion 1385, a second portion 1386, and an inner surface 1387. The first portion 1385 is disposed closer to the upper surface 1380 than the second portion 1386 and defines a second width $w_2'$ that is defined by the inner surface 1387 and is constant from the first proximal side 1372 to the distal side 1374 of the housing 1370. The second width $w_2'$ is sufficiently great to allow the shaft 1250 of the first member 1200 to be rotatably, slidably, and pivotally adjusted within the passageway 1384 of the housing 1370 when the shaft 1250 is engaged with the saddle 1400 and disposed within the passageway 1384. The first portion 1385 of the passageway 1384 is defined by the inner surface 1387 and includes first and second walls 1388, 1389 that are substantially parallel to the longitudinal axis (not illustrated in the Figures) of the housing 1370.

The second portion 1386 of the passageway 1384 tapers from where the second portion 1386 is disposed adjacent the first portion 1385 to where the second portion 1386 is adjacent the void 1394. The second portion 1386, thus, includes a plurality of widths (not illustrated in the Figures). Each of the plurality of widths of the second portion 1386 is less than the second width $w_2'$ in the illustrated embodiment. The second portion 1386 of the passageway 1384 is substantially semi-elliptical in shape and is defined, at various portions, by one or more of the void 1394, the inner surface 1387, the proximal side 1372 of the housing 1370, and the distal side 1374 of the housing 1370. A skilled artisan will be able to determine how to suitably size and shape the first and second portions of the housing according to a particular example on various considerations, including the size and shape of the shaft of the first member and the size and shape of the saddle. In other embodiments, the second width may be less than, substantially equal to, or equal to one or more widths of the second portion. In different embodiments, the first portion may have any other shape, including square, rectangular, triangular, semi-elliptical, and elliptical. In alternative embodiments, the second portion may have any other shape, including square, rectangular, triangular, and elliptical.

The shaft 1350 of the second arm 1300 includes an upper surface 1358, which defines a first width $w_1^{\star\prime}$. As illustrated in the Figures, the second width $w_2'$ is greater than the first width $w_1'$ of the upper surface 1258 of the shaft 1250 of the first arm 1200 and the first width $w_1^{\star\prime}$ of the upper surface 1358 of the shaft 1350 of the second arm 1300. Additionally, at least some of the widths of the second portion 1386 of the passageway 1384 are greater than the first width $w_1'$ in this embodiment. This configuration is advantageous because it allows, for example, the shaft 1250 of the first member 1200 to be pivotally adjusted, after a force is placed on the first member 1200, via rotation of the saddle 1400. The saddle 1400 is disposed within the void 1394 defined by the main body 1371 of the housing 1370, held captive by the tapered inner surface 1395 of the void 1394, and positioned such that it is not able to fall through the void 1394 and lower surface 1382 of the housing 1370. Pivoting force applied to the first member 1200 rotates the saddle 1400 and pivots the first member 1200. Only a certain degree of pivoting is allowed, however, as the proximal and distal sides 1372, 1374 act as a stop to prevent too much pivotal movement of the first member 1200. In addition, as discussed in greater detail below, the shaft 1250 of the first member 1200 also helps to maintain the saddle 1400 within the housing 1370 of the second member 1300. A skilled artisan will be able to determine suitable first widths for the upper surfaces of the shafts of the first and second arms relative to the widths of the first and second portions of the passageway according to a particular example based on various considerations, including the shape and size of the saddle and the desired maximum pivotal adjustment capability. In other embodiments, none of the plurality of widths of the second portion of the passageway is greater than the first width of the shaft of the first member. In different embodiments, each of the plurality of widths of the second portion of the passageway is greater than the first width of the shaft of the first member. In alternative embodiments, the first width of the upper surface of the shaft of the first member can be less than, equal to, or substantially equal to the first width of the upper surface of the second member. Furthermore, the second width may be greater than one or both of the first widths of the shafts of the first and second members by any amount in other embodiments.

FIGS. 13 and 13A illustrate the cross connector 30 in first and second configurations, respectively. In the first configuration, illustrated in FIG. 13, the proximal end 1254 of the shaft 1250 of the first member 1200 is disposed over the shaft 1350 of the second member 1300. FIG. 13A, however, illustrates the second configuration, in which the proximal end 1254 of the shaft 1250 is disposed within the housing 1370. More specifically, the channel 1262 of the proximal end 1254 in which the stop member 1500 is disposed is aligned with the first cavity 1440 of the saddle 1400. The stop member 1500, thus, is disposed within the first cavity 1440 and contacts the side 1452 of the first cavity 1440. This allows the first member 1200 and stop member 1500 to cooperatively exert a force on the saddle 1400 that, along with the tapered inner surface 1395, helps to maintain the saddle 1400 within the void 1394 when the cross connector 30 is in the second configuration. FIG. 13A illustrates the maximum distance between the first and second arms 1202, 1302, as well. A skilled artisan will be able to determine how to suitably configure the stop member, the saddle, and the proximal end of the shaft of the first member according to a particular example based on various configurations, including the size and shape of the stop member and the desired sliding range of motion of the first member relative to the second member. In other embodiments, the stop member may be disposed within the second cavity when the cross connector is in the second configuration. In a different embodiment, a portion of the shaft of the first member, rather than the stop member, may extend into the first cavity. In alternative embodiments, the inner surface of the void may include a notch or cavity into which the stop member may be inserted to further stabilize the stop member within the housing. Alternatively, the first member may not exert a force to help maintain the saddle within the void of the housing in other embodiments.

Figure 19:
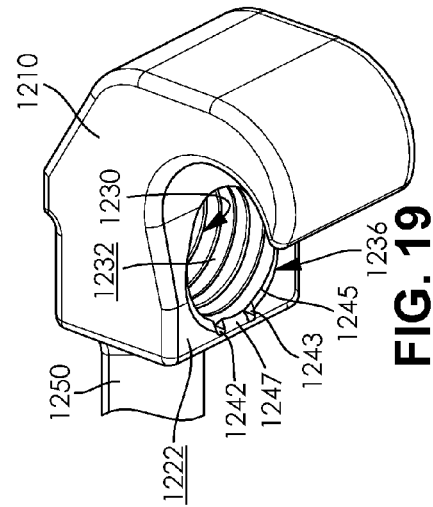
FIG. 19 is another magnified perspective view of Area II of the cross connector illustrated in FIG. 11. The cross connector is illustrated without the set screw illustrated in FIG. 11.
Figure 18:
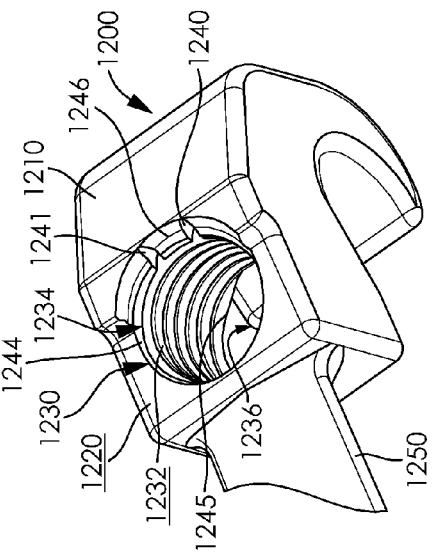
FIG. 18 is a magnified perspective view of Area II of the cross connector illustrated in FIG. 11. The cross connector is illustrated without the set screw illustrated in FIG. 11.

A first arm channel 1230 extends from the upper surface 1220 to the lower surface 1222 of the base 1210 of the first member 1200, as best illustrated in FIGS. 18 and 19. The first arm channel 1230 defines a threaded inner surface 1232, a first opening 1234, and a second opening 1236. The first opening 1234 is defined by the upper surface 1220 and the second opening 1236 is defined by the lower surface 1222. Each of the first and second openings is substantially circular in shape. The first arm channel 1230 is configured to engage a set screw that includes a threaded portion, such as set screw 1700a. The first arm channel 1230 also has a constant diameter from the first opening 1234 to the second opening 1236. A skilled artisan will be able to determine a suitable first arm channel, suitable first and second openings, and a suitable diameter according to a particular example based on various considerations, including the shape and size of the set screw used in conjunction with the first arm channel and the shape and size of the rod that the set screw will engage. In a different embodiment, the first and second openings may be elliptical, square, rectangular, or have any other shape. In another embodiment, the first arm channel may taper or expand from the first opening to the second opening. The first arm channel may also be configured to engage a device other than a set screw.

The inner surface 1232 also includes first, second, third, and fourth slots 1240, 1241, 1242, 1243. The first and second slots 1240, 1241, illustrated in FIG. 18, are disposed adjacent the first opening 1234. The third and fourth slots 1242, 1243 are disposed adjacent the second opening 1236. The first and second slots 1240, 1241 extend toward the second opening 1236 and to the base of the uppermost thread 1244 of the inner surface 1232. A first tab 1246 is formed between the first and second slots 1240, 1241. The third and fourth slots 1242, 1243, illustrated in FIG. 19, extend toward the first opening 1234 and the base of the lowermost thread 1245 of the inner surface 1232. A second tab 1247 is formed between the third and fourth slots 1242, 1243. The first and second tabs 1246, 1247 are configured to maintain a set screw, such as set screw 1700a, within the first arm channel 1230. The first and second slots 1240, 1241 and the first tab 1246 prevent the set screw from escaping the first arm channel 1230 through the first opening 1234 by inhibiting upward movement of the set screw 1700a; the third and fourth slots 1242, 1243 and second tab 1247 prevent the set screw 1700a from escaping the first arm channel 1230 through the second opening 1236 by inhibiting downward movement of the set screw 1700a. Thus, once the set screw 1700a has been inserted into the first arm channel 1230, it is held captive within the first arm channel 1230 by the first and second tabs 1246, 1247. A skilled artisan will be able to determine a suitable number of tabs and slots and their configurations according to a particular example based on various considerations, including the shape and size of the set screw used in conjunction with the first arm channel and the diameter of the first arm channel itself. In other embodiments, zero, one, two, three, five, or more than five tabs may be used. In different embodiments, either of the first and second slots may extend to any depth within the first arm channel. In alternative embodiments, either of the third and fourth slots may extend to any depth within the first arm channel. Additionally, in another alternative, each of the tabs may be configured such that they allow for a set screw to be inserted into one of the first or second openings, but also allow for the set screw to escape the first arm channel without any mechanical change to the tabs after the set screw is placed within the first arm channel. In a different embodiment, one or more of the tabs may be mechanically altered after implantation of the set screw in order to maintain the set screw within the first arm channel. In another embodiment, the tabs may be altered after implantation of the set screw to allow the set screw to be removed from the first arm channel. Additionally, in other embodiments the tabs may include springs that allow for the tabs to recede into the body of the arm upon pressure from a set screw.

A second arm channel 1330 extends from the upper surface 1320 to the lower surface 1322 of the base 1310 of the second member 1300 and is similar to the first arm channel 1230. The second arm channel 1330 defines a threaded inner surface 1332, a first opening 1334, and a second opening 1336. The first opening 1334 is defined by the upper surface 1320 and the second opening 1336 is defined by the lower surface 1322. Each of the first and second openings is substantially circular in shape. The second arm channel 1330 is configured to engage a set screw that includes a threaded portion, such as set screw 1700b. The second arm channel 1330 also has a constant diameter from the first opening 1334 to the second opening 1336. A skilled artisan will be able to determine a suitable second arm channel, suitable first and second openings, and a suitable diameter according to a particular example based on various considerations, including the shape and size of the set screw used in conjunction with the first arm channel and the shape and size of the rod that the set screw will engage. In a different embodiment, the first and second openings may be elliptical, square, rectangular, or have any other shape. In another embodiment, the second arm channel may taper or expand from the first opening to the second opening. The second arm channel may also be configured to engage a device other than a set screw.

The inner surface 1332 also includes first, second, third, and fourth slots (not illustrated in the Figures). The first and second slots are disposed adjacent the first opening 1334. The third and fourth slots are disposed adjacent the second opening 1336. The first and second slots extend toward the second opening 1336 and to the base of the uppermost thread 1344 of the inner surface 1332. A first tab (not illustrated in the Figures) is formed between the first and second slots. The third and fourth slots extend toward the first opening 1334 and the base of the lowermost thread 1245 of the inner surface 1232. A second tab (not illustrated in the Figures) is formed between the third and fourth slots. The first and second tabs are configured to maintain a set screw, such as set screw 1700b, within the second arm channel 1330. The first and second slots and the first tab prevent the set screw 1700b from escaping the second arm channel 1330 through the first opening 1334 by inhibiting upward movement of the set screw 1700b; the third and fourth slots and second tab prevent the set screw 1700b from escaping the second arm channel 1330 through the second opening 1336 by inhibiting downward movement of the set screw 1700b. Thus, once the set screw 1700b has been inserted into the second arm channel 1330, it is held captive within the second arm channel 1330 by the first and second tabs. A skilled artisan will be able to determine a suitable number of tabs and slots and their configurations according to a particular example based on various considerations, including the shape and size of the set screw used in conjunction with the second arm channel and the diameter of the second arm channel itself. In other embodiments, zero, one, two, three, five, or more than five tabs may be used. In different embodiments, either of the first and second slots may extend to any depth within the second arm channel. In alternative embodiments, either of the third and fourth slots may extend to any depth within the second arm channel. Additionally, in another alternative, each of the tabs may be configured such that they allow for a set screw to be inserted into one of the first or second openings, but also allow for the set screw to escape the second arm channel without any mechanical change to the tabs after the set screw is placed within the second arm channel. In a different embodiment, one or more of the tabs may be mechanically altered after implantation of the set screw in order to maintain the set screw within the second arm channel. In another embodiment, the tabs may be altered after implantation of the set screw to allow the set screw to be removed from the second arm channel. Additionally, in other embodiments the tabs may include springs that allow for the tabs to recede into the body of the arm upon pressure from a set screw.

FIG. 20 illustrates an example kit 1800 comprising a cross connector according to an example embodiment, such as cross connector 10 illustrated, for example, in FIG. 1; a set of rods 1900a, 1900b; a set of anchors 2000a, 2000b; and a set of anchor heads 2100a, 2100b. In other embodiments, another cross connector may be used, including one of cross connectors 20 or 30.

While a single cross connector 10 is illustrated in FIG. 16, multiple cross connectors may be included in the kit 1800, as well. In addition, more or fewer than two rods, anchors, and anchor heads may be included in the kit and a single rod, anchor, or anchor head may be sized and shaped differently than any other single rod, anchor, or anchor head. A skilled artisan will be able to select a suitable number of cross connectors, rods, anchors, and anchor heads based on various considerations, including the location in the body at which the cross connector will be implanted.

FIG. 21 is a flowchart representation of an example method 2200 of engaging a cross connector with at least one rod. Performance of this method results in the engagement of the cross connector with the at least one rod. This method can be used for engaging any type of cross connector with any type of rod. The rod may or may not be implanted within the body prior to the performance of this method 2200.

An initial step 2202 comprises identifying at least one suitable rod to engage with the cross connector 30. Rods 1900a, 1900b are described in this step 2202. In other methods, other rods or devices other than rods may be identified. Cross connector 30 is described in this step. In other methods, other cross connectors, such as cross connectors 10 or 20, for example, may be described.

Another step 2204 comprises engaging rod 1900a with the arm 1302 of the second member 1300 through the use of a set screw 1700b. In other methods, the arm of the first member may engage the rod in this step. In different methods, the arm may engage a device other than a rod. Alternatively, a device other than a set screw may be used to engage the rod with the arm of the second member.

Another step 2206 comprises engaging rod 1900b with the arm 1202 of the first member 1200 through the use of a set screw 1700a. In other methods, the arm of the second member may engage the rod in this step. In different methods, the arm may engage a device other than a rod. Alternatively, a device other than a set screw may be used to engage the rod with the arm of the second member.

Another step 2208 comprises suitably adjusting the shaft 1250 of the first member 1200 slidably, rotatably, and pivotally within the housing 1370 of the second member 1300. The arms 1202, 1302 continue to engage the first and second rods 1900b, 1900a, respectively. Step 2208 may be performed via manual adjustment of the shaft 1250 or through mechanical adjustment of the shaft 1250. In other methods, the arm of the first member may be adjusted rather than the shaft.

Another step 2210 comprises tightening the locking member 1600 within the channel 1390 of the housing 1370 such that the locking member 1600 is in contact with the shaft 1250 of the first member 1200 and holds the first member 1200 in place.

It is noted that the method 2200 may be completed in the order illustrated and described. However, the steps may also be completed in any order.

The cross connectors, kits, and methods are useful in a variety of orthopedic procedures. Particular embodiments, including the specific embodiments illustrated and described in detail herein, are useful in a variety of orthopedic procedures.

All components of the cross connectors, kits, and methods, can be made from any suitable material. Non-limiting examples of suitable materials include metals, such as stainless steel, titanium, cobalt-chromium, and other metals, plastics commonly used in medical devices, Nitinol and other superelastic materials, polyurethane materials, silicone materials, and polyether ether ketone (PEEK) materials.

Those with ordinary skill in the art will appreciate that various modifications and alternatives for the described and illustrated embodiments can be developed in light of the overall teachings of the disclosure. Accordingly, the particular arrangements disclosed are intended to be illustrative only and not limiting as to the scope of the invention, which is to be given the full breadth of the appended claims and all equivalents thereof.

We claim:

1. A cross connector configured to engage at least one medical device, comprising:
    a first member having an arm and a shaft, the arm being configured to engage one of said at least one medical device, the shaft having an upper surface and a lower surface, the shaft defining a channel extending from the upper surface to the lower surface, the upper surface of the shaft having a first width;
    a second member having an arm, a housing, and a shaft, the shaft extending from the arm to the housing, the shaft having an upper surface, the arm being configured to engage one of said at least one medical device, the housing having a proximal side, a distal side, an upper surface, a passageway, a channel, and a void, the passageway extending from the proximal side to the distal side and defining a first opening and a second opening, the first opening having a second width, the channel at least partially defined by the upper surface and in communication with the passageway, the void in communication with the passageway, the shaft of the first member disposed within the passageway such that the first member is rotatably, pivotally, and slidably moveable within the passageway;
    a saddle, the saddle housed within the void of the housing of the second member and configured to engage the shaft of the first member, the saddle being rotatable;
    a stop member, the stop member disposed within the channel of the shaft of the first member; and
    a locking member, the locking member disposed within the channel of the housing of the second member such that the locking member is in contact with the upper surface of the shaft of the first member;
    wherein the first width is less than the second width.

2. The cross connector of claim 1, wherein the shaft of the second member includes a lower surface, a first lateral side, a second lateral side, a first rounded portion disposed adjacent the upper surface and the first lateral side, and a second rounded portion disposed adjacent the upper surface and the second lateral side.

3. The cross connector of claim 1, wherein the housing includes a first lateral side and a second lateral side;
    wherein the housing includes a first rounded portion adjacent the first lateral side and the upper surface of the housing;
    wherein the housing includes a second rounded portion adjacent the second lateral side and the upper surface of the housing;
    wherein the housing includes a third rounded portion adjacent the proximal side and the upper surface of the housing; and
    wherein the housing includes a fourth rounded portion adjacent the distal side and the upper surface of the housing.

4. The cross connector of claim 3, wherein the proximal side of the housing, the distal side of the housing, the first lateral side of the housing, and the second lateral side of the housing are substantially rounded rectangular in shape.

5. The cross connector of claim 1, wherein the arm of the first member has an upper arm surface and a lower arm surface; and
    wherein the arm of the first member defines a first arm channel extending from the upper arm surface to the lower arm surface.

6. The cross connector of claim 5, wherein the arm of the second member has an upper arm surface and a lower arm surface; and
    wherein the arm of the second member defines a second arm channel extending from the upper arm surface to the lower arm surface.

7. The cross connector of claim 6, wherein the first arm channel is disposed at a first angle relative to a plane containing the upper surface of the shaft of the first member;
    wherein the second arm channel is disposed at a second angle relative to a plane containing the upper surface of the shaft of the first member; and
    wherein the first angle is different than the second angle.

8. The cross connector of claim 7, further comprising a first set screw disposed within the first arm channel.

9. The cross connector of claim 8, further comprising a second set screw disposed within the second arm channel.

10. The cross connector of claim 9, wherein the upper surface of the first member is faceted.

11. The cross connector of claim 10, wherein the channel defined by the shaft of the first member has an upper opening and a lower opening; and
    wherein the upper surface of the first member defines an indented portion adjacent the upper opening.

12. The cross connector of claim 1, wherein the at least one medical device comprises a rod.

13. The cross connector of claim 1, wherein the saddle has an upper surface, a lower surface, and a side that tapers from the upper surface to the lower surface.

14. The cross connector of claim 13, wherein the side and the upper surface of the saddle cooperatively define a first cavity.

15. The cross connector of claim 14, wherein the side and the upper surface of the saddle cooperatively define a second cavity.

16. The cross connector of claim 14, wherein the stop member is disposed within the first cavity.

17. The cross connector of claim 1, wherein the stop member is disposed adjacent the upper surface of the shaft of the second member, and between the housing and arm of the second member.

18. A cross connector configured to engage at least one medical device, comprising:
    a first member having an arm and a shaft, the arm being configured to engage one of said at least one medical device, the arm having an upper arm surface and a lower arm surface, the arm defining a first arm channel extending from the upper arm surface to the lower arm surface, the shaft having an upper surface and a lower surface, the shaft defining a channel extending from the upper surface to the lower surface, the upper surface of the shaft having a first width;
    a second member having an arm, a housing, and a shaft, the shaft extending from the arm to the housing, the shaft having an upper surface, the arm being configured to engage one of said at least one medical device, the arm having an upper arm surface and a lower arm surface, the arm defining a second arm channel extending from the upper arm surface to the lower arm surface, the housing having a proximal side, a distal side, an upper surface, a passageway, a channel, and a void, the passageway extending from the proximal side to the distal side and defining a first opening and a second opening, the first opening having a second width, the channel at least partially defined by the upper surface and in communication with the passageway, the void in communication with the passageway, the shaft of the first member disposed within the passageway such that the first member is rotatably, pivotally, and slidably moveable within the passageway;

a saddle, the saddle housed within the void of the housing of the second member and configured to engage the shaft of the first member, the saddle being rotatable and having an upper surface, a lower surface, and a side that tapers from the upper surface to the lower surface, the side and the upper surface cooperatively defining first and second cavities;

a stop member, the stop member disposed within the channel of the shaft of the first member; and a locking member, the locking member disposed within the channel of the housing of the second member such that the locking member is in contact with the upper surface of the shaft of the first member;

wherein the first width is less than the second width.

19. The cross connector of claim 18, wherein the stop member is disposed within the first cavity.

20. A cross connector configured to engage at least one medical device, comprising:

a first member having an arm and a shaft, the arm being configured to engage one of said at least one medical device, the arm having an upper arm surface and a lower arm surface, the arm defining a first arm channel extending from the upper arm surface to the lower arm surface, the shaft having an upper surface and a lower surface, the shaft defining a channel extending from the upper surface to the lower surface, the upper surface of the shaft having a first width;

a second member having an arm, a housing, and a shaft, the shaft extending from the arm to the housing, the shaft having an upper surface, the arm being configured to engage one of said at least one medical device, the arm having an upper arm surface and a lower arm surface, the arm defining a second arm channel extending from the upper arm surface to the lower arm surface, the housing having a proximal side, a distal side, an upper surface, a passageway, a channel, and a void, the passageway extending from the proximal side to the distal side and defining a first opening and a second opening, the first opening having a second width, the channel at least partially defined by the upper surface and in communication with the passageway, the void in communication with the passageway, the shaft of the first member disposed within the passageway such that the first member is rotatably, pivotally, and slidably moveable within the passageway;

a saddle, the saddle housed within the void of the housing of the second member and configured to engage the shaft of the first member, the saddle being rotatable and having an upper surface, a lower surface, and a side that tapers from the upper surface to the lower surface, the side and the upper surface cooperatively defining first and second cavities;

a stop member, the stop member disposed within the channel of the shaft of the first member;

a locking member, the locking member disposed within the channel of the housing of the second member such that the locking member is in contact with the upper surface of the shaft of the first member;

a first set screw disposed within the first arm channel; and a second set screw disposed within the second arm channel;

wherein the first width is less than the second width.

* * * * *